United States Patent
Marrone et al.

(10) Patent No.: US 12,002,555 B2
(45) Date of Patent: Jun. 4, 2024

(54) ELECTRONIC HEALTHCARE FORM GENERATION WITH BUNDLED SUPPLEMENTAL DOCUMENTATION

(71) Applicant: SWELLBOX, INC., Tarrytown, NY (US)

(72) Inventors: Jeffrey Marrone, Elmwood Park, NJ (US); Brian Korb, Irvington, NY (US); Jefferson Seidl, New York, NY (US); Sean Wright, Media, PA (US)

(73) Assignee: DATAVANT, INC., Phoenix, AZ (US)

( * ) Notice: Subject to any disclaimer, the term of this patent is extended or adjusted under 35 U.S.C. 154(b) by 855 days.

(21) Appl. No.: 17/025,556

(22) Filed: Sep. 18, 2020

(65) Prior Publication Data

US 2021/0090696 A1 Mar. 25, 2021

Related U.S. Application Data

(60) Provisional application No. 62/903,340, filed on Sep. 20, 2019.

(51) Int. Cl.
*G16H 10/60* (2018.01)
*G16H 30/20* (2018.01)
*G16H 30/40* (2018.01)

(52) U.S. Cl.
CPC ............. *G16H 10/60* (2018.01); *G16H 30/20* (2018.01); *G16H 30/40* (2018.01)

(58) Field of Classification Search
CPC ........ G16H 10/60; G16H 30/20; G16H 30/40; G16H 80/00; G16H 10/20
See application file for complete search history.

(56) References Cited

U.S. PATENT DOCUMENTS

| | | | |
|---|---|---|---|
| 8,073,711 | B1 | 12/2011 | McCollum et al. |
| 9,411,823 | B1 * | 8/2016 | Rice ...................... G06F 16/50 |
| 2017/0011192 | A1 | 1/2017 | Arshad et al. |
| 2017/0249424 | A1 | 8/2017 | Augusto Di Grandi Nery et al. |
| 2018/0360295 | A1 | 12/2018 | Boucher et al. |

OTHER PUBLICATIONS

Ventola CL. Mobile devices and apps for health care professionals: uses and benefits. P T. May 2014;39(5):356-64. PMID: 24883008; PMCID: PMC4029126. (Year: 2014).*
Emory Healthcare; Medical Records and Release of Information webpage; archived Aug. 26, 2019 (Year: 2019).*
Cottage Health, "Accessing Your Medical Records", <https://www.cottagehealth.org/patients-visitors/accessing-your-medical-records/>, Sep. 15, 2017.

(Continued)

*Primary Examiner* — Joshua B Blanchette
(74) *Attorney, Agent, or Firm* — Lando & Anastasi, LLP

(57) ABSTRACT

Techniques for generating healthcare form bundles with supplemental live image documentation are disclosed. The techniques include: obtaining, from a user, values of fields of a healthcare form; capturing a live image including supplemental documentation for the healthcare form, from a camera of a device operated by the user; generating a form bundle including (a) an electronic version of the healthcare form populated with the values, and (b) the image including the supplemental documentation for the healthcare form; and transmitting the form bundle to a healthcare organization.

15 Claims, 43 Drawing Sheets

(56) References Cited

OTHER PUBLICATIONS

Emory Healthcare, "Medical Records and Release of Information", <https://www.emoryhealthcare.org/patients-visitors/medical-records.html>, Aug. 26, 2019.
International Search Report and Written Opinion from corresponding International Application No. PCT/US2020/051621 dated Dec. 22, 2020.
Sutter Health, "Request Your Medical Records", <https://www.sutterhealth.org/for-patients/request-medical-record>, Jul. 3, 2019.
TRIMSNet—eRequest LLC Product page, <https://e-requestllc.com/Products> [retrieved on Jan. 4, 2021].

* cited by examiner

300

Medical Record Number: _____
*(for internal purposes)*

PROVIDER HEALTHCARE

AUTHORIZATION FOR THE RELEASE OF PROTECTED HEALTH INFORMATION
HEALTH INFORMATION MANAGEMENT DEPARTMENT

Patient Name: _____ Last 4 digits of SSN: _____
Previous Name, if applicable: _____
Address: _____ City: _____ State: _____ Zip Code: _____
Date of Birth: _____ Home Phone: _____ Work Phone: _____
Email address: _____

1. PROVIDER HEALTHCARE FACILITY/FACILITIES:
   I authorize representatives from the following facility/facilities to disclose the health information as directed below:
   (Check one or more):
   - ☐ Facility A
   - ☐ Facility B
   - ☐ Facility C
   - ☐ Facility D
   - ☐ Facility E
   - ☐ Facility F
   - ☐ Facility G
   - ☐ Facility H
   - ☐ Facility I
   - ☐ Facility J
   - ☐ Facility K
   - ☐ Facility L
   - ☐ Facility M
   - ☐ Facility N
   - ☐ Facility O
   - ☐ Facility P
   - ☐ Facility Q
   - ☐ Other: _____

2. RECEIVING PARTY, FORMAT, AND METHOD OF DELIVERY:
   FORMAT:
   - ☐ On Paper
   - ☐ On CD
   - ☐ Flash Drive METHOD OF DELIVERY:
   - ☐ Mail (Complete info below)
   - ☐ Pick up (List by whom below)
   - ☐ EHC Electronic Release of Information Request Website (In order to receive records via the electronic website, you must create an account through the website, then submit your request via the website. Please see attached instructions)
   - ☐ Via Email (Please provide email address above) Please note, due to file size limits for our organization, records sent via email are restricted to a small number of pages.

Name: _____
   Address: _____
   City: _____ State: _____ Zip Code: _____
   Telephone Number: _____
   Fax Number (continuing patient care support only): _____

3. DESCRIPTION OF HEALTH INFORMATION TO BE DISCLOSED:
   - ☐ Complete medical record *(Please specify dates of service)* _____
     OR
   - ☐ Partial Medical Record *(Please specify records below)*
   - ☐ Continuity of Care/Abstract *(please specify dates of service)* _____
   - ☐ You must check this box if you are also requesting Billing Records

| Information | Dates | Information | Dates |
   |---|---|---|---|
   | ☐ History & physical | _____ | ☐ Office notes/Progress notes | _____ |
   | ☐ Consultations | _____ | ☐ Operative reports | _____ |
   | ☐ Discharge summary | _____ | ☐ Pathology reports | _____ |
   | ☐ Lab results | _____ | ☐ Pathology slides | _____ |
   | ☐ X-rays | _____ | ☐ EKG reports | _____ |
   | ☐ CD/Films | _____ | ☐ Photo/Videos | _____ |
   | ☐ Cath Record | _____ | ☐ ED Record | _____ |
   | ☐ Itemized Bill | _____ | ☐ Rhythm Strips | _____ |
   | ☐ Other *(Please specify dates of service):* _____ | | ☐ Pathology Slides | _____ |

4. PURPOSE OF DISCLOSURE
   - ☐ At my request    Need Records Certified ☐ Yes ☐ No
   - ☐ Other: _____

Front

FIG. 3A

[PROVIDER LOGO]

What is your full legal name?

This should be your name when you visited this provider (maiden name, or other).

FIRST NAME: Skyler

LAST NAME: Jones

MIDDLE INITIAL:

☐ Check this box if your name has changed.

[ Next ]

Medical Record Number: _____
*(for internal purposes)*

PROVIDER HEALTHCARE

AUTHORIZATION FOR THE RELEASE OF PROTECTED HEALTH INFORMATION
HEALTH INFORMATION MANAGEMENT DEPARTMENT

Patient Name: Skyler Jones                                      Last 4 digits of SSN: _____
Previous Name, if applicable: _____
Address: 1 Main Street            City: Petaluma            State: CA    Zip Code: 94952
Date of Birth: 01/01/1951         Home Phone: (111) 111-1111    Work Phone: _____
Email address: example@example.com 1. PROVIDER HEALTHCARE FACILITY/FACILITIES:
   I authorize representatives from the following facility/facilities to disclose the health information as directed below:
   (Check one or more):
   - ☒ Facility A
   - ☐ Facility B
   - ☐ Facility C
   - ☐ Facility D
   - ☐ Facility E
   - ☐ Facility F
   - ☐ Facility G
   - ☐ Facility H
   - ☐ Facility I
   - ☐ Facility J
   - ☐ Facility K
   - ☐ Facility L
   - ☐ Facility M
   - ☐ Facility N
   - ☐ Facility O
   - ☐ Facility P
   - ☐ Facility Q
   - ☐ Other: _____

2. RECEIVING PARTY, FORMAT, AND METHOD OF DELIVERY:
   FORMAT:
   - ☒ On Paper
   - ☐ On CD
   - ☐ Flash Drive METHOD OF DELIVERY:
   - ☒ Mail (Complete info below)
   - ☐ Pick up (List by whom below)
   - ☐ EHC Electronic Release of Information Request Website (In order to receive records via the electronic website, you must create an account through the website, then submit your request via the website. Please see attached instructions)
   - ☐ Via Email (Please provide email address above) Please note, due to file size limits for our organization, records sent via email are restricted to a small number of pages.

Name: Doctor, M.D.
   Address: 1 Medical Way
   City: Petaluma            State: CA    Zip Code: 94952
   Telephone Number: _____
   Fax Number (continuing patient care support only): _____

3. DESCRIPTION OF HEALTH INFORMATION TO BE DISCLOSED:
   - ☐ Complete medical record *(Please specify dates of service)* _____
   OR
   - ☒ Partial Medical Record *(Please specify records below)*
   - ☒ Continuity of Care/Abstract *(please specify dates of service)* 09/11/2019 to 09/11/2020
   - ☐ You must check this box if you are also requesting Billing Records

| Information | Dates | Information | Dates |
   |---|---|---|---|
   | ☐ History & physical | | ☐ Office notes/Progress notes | |
   | ☐ Consultations | | ☐ Operative reports | |
   | ☐ Discharge summary | | ☐ Pathology reports | |
   | ☐ Lab results | | ☐ Pathology slides | |
   | ☐ X-rays | | ☐ EKG reports | |
   | ☐ CD/Films | | ☐ Photo/Videos | |
   | ☐ Cath Record | | ☐ ED Record | |
   | ☐ Itemized Bill | | ☐ Rhythm Strips | |
   | ☐ Other *(Please specify dates of service)*: | | ☐ Pathology Slides | |

4. PURPOSE OF DISCLOSURE
   - ☐ At my request    Need Records Certified ☐ Yes ☐ No
   - ☒ Other: Patient Request Front
\*\*REQUESTOR DECLINES SENSITIVE RECORDS\*\*

FIG. 3LL

Skyler Jones (D.O.B. 01/01/1951)

Additional Identifiers Requested

1. Driver's License 2020-09-11 07:34:40 PM EDT

2. Mailing Address
1 Main Street
Petaluma, CA 94952

3. Email Address (user confirmed)
example@example.com (consented to an unencrypted emailed copy of their request)

4. Phone Number (verified)
(111) 111-1111

5. Signature

REASON FOR REQUEST
Patient Request

ELECTRONIC HEALTHCARE FORM GENERATION WITH BUNDLED SUPPLEMENTAL DOCUMENTATION

RELATED APPLICATIONS

This application claims the benefit of U.S. Provisional Patent Application Ser. No. 62/903,340, titled "System for Electronically Completing and Submitting Forms in Healthcare Without Disrupting Existing Workflow Processes," filed Sep. 20, 2019, which is hereby incorporated by reference in its entirety for all purposes.

BACKGROUND

Healthcare organizations use forms for many different purposes. For example, healthcare organizations may use forms to obtain authorizations to release medical records (e.g., to patients, caregivers, other healthcare organizations, lawyers, insurers, etc.) and/or for many other purposes. In the United States, some forms used by healthcare organizations are required by the Health Insurance Portability and Accountability Act of 1996 (HIPAA). In the following discussion, a person completing a form is referred to as a "requestor," because the person is requesting that a healthcare organization take some action with respect to the information indicated on the form. For example, the person may be a patient or legal guardian requesting that the healthcare organization release medical records identified in a HIPAA authorization/release form or proceed with some other course of action for which the healthcare organization requires a completed form. Different healthcare organizations may use different forms for the same or similar purposes.

Some forms require requestors to provide supplemental documentation. For example, some forms require documentation of medical power of attorney (POA), photo identification (ID), health insurance documentation (e.g., a health insurance card), and/or other supplemental documentation.

Traditional methods of providing supplemental documentation to healthcare organizations are time-consuming (e.g., hand delivery) and/or insecure (e.g. fax or unsecured email). In addition, traditional methods of providing supplemental documentation are prone to mismatch or loss, due to the supplemental documentation being submitted at a different time than the form itself, submitted in a different format than the form itself, and/or physically disconnected from the form itself. Traditional methods of providing supplemental documentation may require access to equipment that is not readily available, such as a fax machine.

Successfully processing a form requires that the form be completed thoroughly and accurately. Legible responses must be supplied for required fields, and the required supplemental documentation must be provided. An incomplete or illegible form may require the healthcare organization to take the time to contact the requestor, who must then take the time to complete the form again and/or supply the missing supplemental documentation. In some cases, an incomplete or illegible form may delay medical treatment, cause the requestor to miss a legal deadline, or otherwise harm (physically, financially, and/or otherwise) the requestor, the healthcare organization, and/or a third party.

Approaches described in this section have not necessarily been conceived and/or pursued prior to the filing of this application. Accordingly, unless otherwise indicated, approaches described in this section should not be construed as prior art.

TECHNICAL FIELD

This application generally relates to managing healthcare data. In particular, this application relates to completing and submitting forms in healthcare.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures.

DETAILED DESCRIPTION

Figure 1:
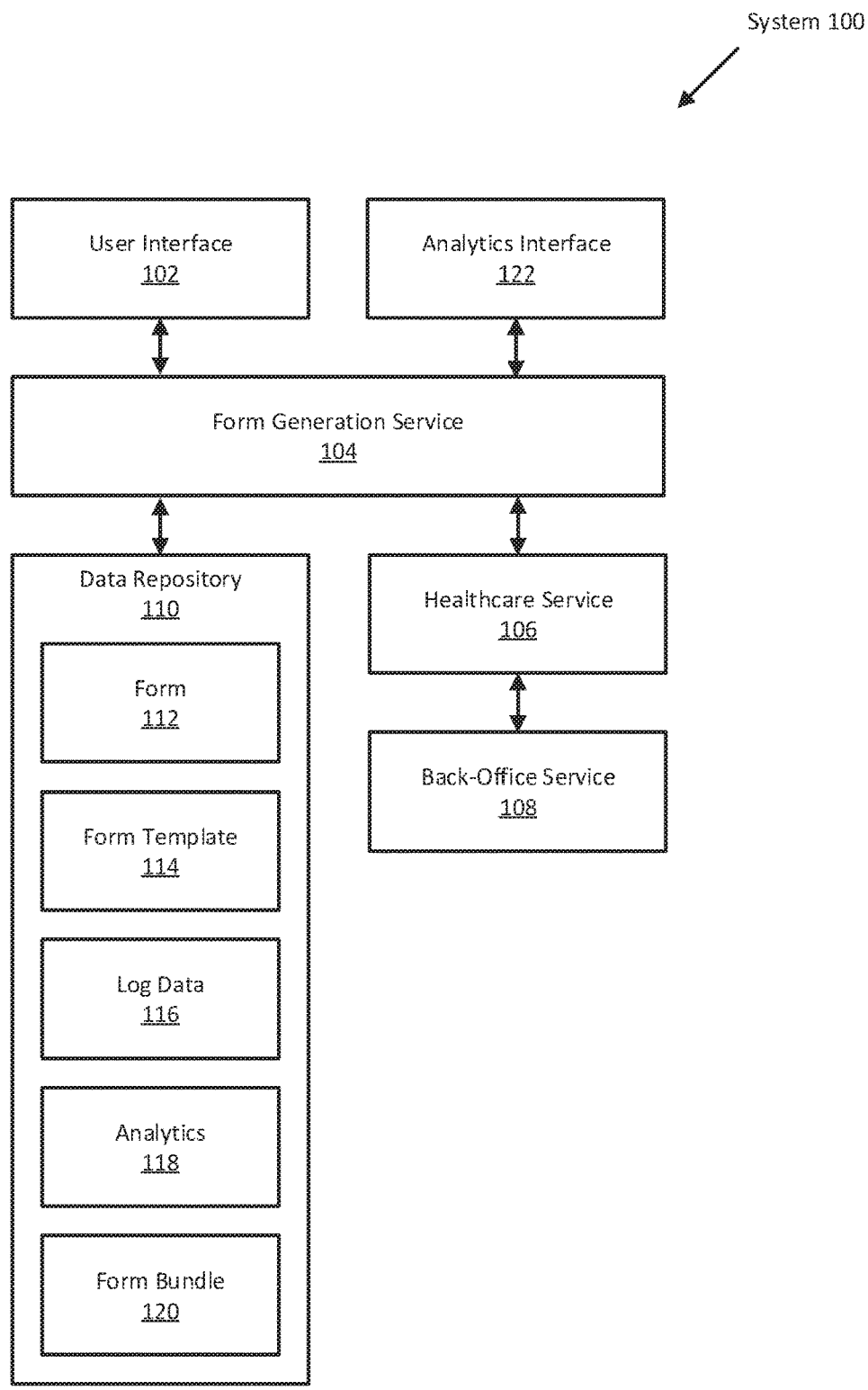
FIG. 1 is a block diagram of an example of a system according to an embodiment.

The following table of contents is provided for the reader's convenience and is not intended to define the limits of the disclosure.

1. GENERAL OVERVIEW
2. SYSTEM ARCHITECTURE
3. COMPLETING AND SUBMITTING A FORM
4. DETAILED EXAMPLES
5. MISCELLANEOUS; EXTENSIONS
6. COMPUTING DEVICES
7. COMPUTER NETWORKS

1. General Overview

In general, in one aspect, one or more non-transitory computer-readable media store instructions that, when executed by one or more processors, cause performance of operations including: obtaining, from a user, values of fields of a healthcare form; capturing a live image including supplemental documentation for the healthcare form, from a camera of a first device operated by the user; generating a form bundle including (a) an electronic version of the healthcare form populated with the values, and (b) the image including the supplemental documentation for the healthcare form; and transmitting the form bundle to a healthcare organization. The first device operated by the user may be a mobile device.

Obtaining the values of fields of the healthcare form may include obtaining at least a subset of the values via a user interface of a second device operated by the user.

The operations may further include: responsive to user input to the user interface of the second device, sending a message to the first device including a link to a website for capturing the live image.

The operations may further include: obtaining, via the user interface of the second device, contact information associated with the first device; and initiating an authentication process for the contact information associated with the first device, wherein sending the message to the first device is performed only upon successful completion of the authentication process for the contact information associated with the first device. Obtaining the values of fields of the healthcare form may include obtaining the contact information associated with the first device.

The operations may further include: transferring a workflow for preparing the form bundle from the user interface of the second device to a user interface of the first device, wherein transmitting the form bundle to the healthcare organization is performed responsive to user input to the user interface of the first device.

In general, in one aspect, a system includes at least one device including a hardware processor. The system may be configured to perform operations including: obtaining, from a user, values of fields of a healthcare form; capturing a live image including supplemental documentation for the healthcare form, from a camera of a first device operated by the user; generating a form bundle including (a) an electronic version of the healthcare form populated with the values, and (b) the image including the supplemental documentation for the healthcare form; and transmitting the form bundle to a healthcare organization. The first device operated by the user may be a mobile device.

Obtaining the values of fields of the healthcare form may include obtaining at least a subset of the values via a user interface of a second device operated by the user.

The operations may further include: responsive to user input to the user interface of the second device, sending a message to the first device including a link to a website for capturing the live image.

The operations may further include: obtaining, via the user interface of the second device, contact information associated with the first device; and initiating an authentication process for the contact information associated with the first device, wherein sending the message to the first device is performed only upon successful completion of the authentication process for the contact information associated with the first device. Obtaining the values of fields of the healthcare form may include obtaining the contact information associated with the first device.

The operations may further include: transferring a workflow for preparing the form bundle from the user interface of the second device to a user interface of the first device, wherein transmitting the form bundle to the healthcare organization is performed responsive to user input to the user interface of the first device.

In general, in one aspect, a method includes: obtaining, from a user, values of fields of a healthcare form; capturing a live image including supplemental documentation for the healthcare form, from a camera of a first device operated by the user; generating a form bundle including (a) an electronic version of the healthcare form populated with the values, and (b) the image including the supplemental documentation for the healthcare form; and transmitting the form bundle to a healthcare organization. The first device operated by the user may be a mobile device.

Obtaining the values of fields of the healthcare form may include obtaining at least a subset of the values via a user interface of a second device operated by the user. The method may further include: responsive to user input to the user interface of the second device, sending a message to the first device including a link to a website for capturing the live image.

The method may further include: obtaining, via the user interface of the second device, contact information associated with the first device; and initiating an authentication process for the contact information associated with the first device, wherein sending the message to the first device is performed only upon successful completion of the authentication process for the contact information associated with the first device. Obtaining the values of fields of the healthcare form may include obtaining the contact information associated with the first device.

The method may further include: transferring a workflow for preparing the form bundle from the user interface of the second device to a user interface of the first device, wherein transmitting the form bundle to the healthcare organization is performed responsive to user input to the user interface of the first device.

In general, in one aspect, one or more non-transitory computer-readable media store instructions that, when executed by one or more processors, cause performance of operations including: receiving, via a user interface, structured data for a form; receiving, via the user interface, unstructured data corresponding to supplemental documentation for the form; generating a form bundle including at least the structured data and the unstructured data; and transmitting the form bundle to a healthcare organization.

Transmitting the form bundle to the healthcare organization may be performed responsive to user input to submit the form, and the operation may further include, responsive to the user input to submit the form, also transmitting the form bundle to a requestor of the form. Transmitting the form bundle to the requestor of the form may include replacing first destination data associated with the healthcare organization in the form bundle with second destination data associated with the requestor.

The operations may further include, responsive to user input indicating a reason for completing the form: preselecting one or more options in the form.

The operations may further include, responsive to user input indicating a deadline for completing the form: transmitting an alert associated with the deadline to the healthcare organization.

The operations may further include: obtaining verified mobile contact information of a requestor of the form; and after transmitting the form bundle to the healthcare organization:

transmitting a status notification, indicating a status of processing the form by the healthcare organization, to the requestor via the verified mobile contact information.

The operations may further include: obtaining user feedback associated with the user interface; storing the user feedback in aggregated user feedback; and generating analytics based on the aggregated user feedback.

Generating the form bundle may include populating the form with the structured data. The form may be a fillable form and populating the form with the structured data may be based on a form template that maps structured data elements to corresponding form field input names in the fillable form. The form may be a fillable form and populating the form may include performing natural language processing on the structured data to map structured data elements to corresponding form field input names in the fillable form. Generating the form bundle may further include flattening the form to remove layering information.

The form bundle may further include an audit trail page.

Transmitting the form bundle to the healthcare organization may include packaging the form bundle in a data structure including (a) elements storing the structured data and (b) an element storing an encoded version of the form.

The healthcare organization uses identification data in the form bundle to perform an automated records lookup via an application programming interface (API) of a back-office service.

The operations may further include generating aggregate analytics based on multiple uses of the user interface.

In general, in one aspect, a system includes at least one device including a hardware processor. The system may be configured to perform operations including: receiving, via a user interface, structured data for a form; receiving, via the user interface, unstructured data corresponding to supplemental documentation for the form; generating a form bundle including at least the structured data and the unstructured data; and transmitting the form bundle to a healthcare organization.

Transmitting the form bundle to the healthcare organization may be performed responsive to user input to submit the form, and the operation may further include, responsive to the user input to submit the form, also transmitting the form bundle to a requestor of the form. Transmitting the form bundle to the requestor of the form may include replacing first destination data associated with the healthcare organization in the form bundle with second destination data associated with the requestor.

The operations may further include, responsive to user input indicating a reason for completing the form: preselecting one or more options in the form.

The operations may further include, responsive to user input indicating a deadline for completing the form: transmitting an alert associated with the deadline to the healthcare organization.

The operations may further include: obtaining verified mobile contact information of a requestor of the form; and after transmitting the form bundle to the healthcare organization: transmitting a status notification, indicating a status of processing the form by the healthcare organization, to the requestor via the verified mobile contact information.

The operations may further include: obtaining user feedback associated with the user interface; storing the user feedback in aggregated user feedback; and generating analytics based on the aggregated user feedback.

Generating the form bundle may include populating the form with the structured data. The form may be a fillable form and populating the form with the structured data may be based on a form template that maps structured data elements to corresponding form field input names in the fillable form. The form may be a fillable form and populating the form may include performing natural language processing on the structured data to map structured data elements to corresponding form field input names in the fillable form. Generating the form bundle may further include flattening the form to remove layering information.

The form bundle may further include an audit trail page.

Transmitting the form bundle to the healthcare organization may include packaging the form bundle in a data structure including (a) elements storing the structured data and (b) an element storing an encoded version of the form.

The healthcare organization uses identification data in the form bundle to perform an automated records lookup via an application programming interface (API) of a back-office service.

The operations may further include generating aggregate analytics based on multiple uses of the user interface.

In general, in one aspect, a method includes: receiving, via a user interface, structured data for a form; receiving, via the user interface, unstructured data corresponding to supplemental documentation for the form; generating a form bundle including at least the structured data and the unstructured data; and transmitting the form bundle to a healthcare organization.

Transmitting the form bundle to the healthcare organization may be performed responsive to user input to submit the form, and the operation may further include, responsive to the user input to submit the form, also transmitting the form bundle to a requestor of the form. Transmitting the form bundle to the requestor of the form may include replacing first destination data associated with the healthcare organization in the form bundle with second destination data associated with the requestor.

The method may further include, responsive to user input indicating a reason for completing the form: preselecting one or more options in the form.

The method may further include, responsive to user input indicating a deadline for completing the form: transmitting an alert associated with the deadline to the healthcare organization.

The method may further include: obtaining verified mobile contact information of a requestor of the form; and after transmitting the form bundle to the healthcare organization: transmitting a status notification, indicating a status of processing the form by the healthcare organization, to the requestor via the verified mobile contact information.

The method may further include: obtaining user feedback associated with the user interface; storing the user feedback in aggregated user feedback; and generating analytics based on the aggregated user feedback.

Generating the form bundle may include populating the form with the structured data. The form may be a fillable form and populating the form with the structured data may be based on a form template that maps structured data elements to corresponding form field input names in the fillable form. The form may be a fillable form and populating the form may include performing natural language processing on the structured data to map structured data elements to corresponding form field input names in the fillable form. Generating the form bundle may further include flattening the form to remove layering information.

The form bundle may further include an audit trail page.

Transmitting the form bundle to the healthcare organization may include packaging the form bundle in a data structure including (a) elements storing the structured data and (b) an element storing an encoded version of the form.

The healthcare organization uses identification data in the form bundle to perform an automated records lookup via an application programming interface (API) of a back-office service.

The method may further include generating aggregate analytics based on multiple uses of the user interface.

One or more embodiments described in this Specification and/or recited in the claims may not be included in this General Overview section.

2. System Architecture

One or more embodiments include a system (e.g., an embodiment of the example system described below) that is configured to generate a form bundle, which includes both structured and unstructured data. The structured data includes a digital form completed to a healthcare organization's specifications (e.g., conforming to the healthcare organization's own forms). The digital form is "structured" in the sense that it includes predefined locations (i.e., a form structure) for particular field values such as name, contact information, etc. The structured nature of the form may allow for the completion of a digital version of the form with the same layout as a form completed on paper. Thus, a healthcare provider can continue to work with a preexisting form, regardless of whether each completed instance of the form is provided on paper or digitally. This approach allows healthcare providers to avoid the considerable overhead associated with attempting to switch to a form that is standardized across multiple providers.

The unstructured data includes supplemental documentation associated with the form (e.g., photo identification, medical power of attorney, insurance information, etc.). The supplemental documentation is "unstructured" in the sense that it exists outside the predefined structure of the form. The supplemental documentation may not be readily susceptible to being mapped to a predefined structured layout, and/or it may not be necessary to do so.

In an embodiment, the system is configured to receive user input from a user interface to complete the digital form. As shown in examples below, the user interface may present a user-friendly, step-by-step 'wizard' that guides the user through a process of completing the form and providing supplemental documentation. To generate the structured data, the system may populate a form with user input corresponding to values of the fields of the form. In addition to populating user-supplied values of fields, the system may be configured to receive user input to electronically sign the digital form and/or supplemental documentation. The system may be configured to receive an electronic signature via desktop computer, laptop, smartphone, tablet, and/or one or more other types of devices.

In an embodiment, the system is configured to verify a user's mobile contact information (e.g., mobile phone number, an email address linked to a messaging system such as Apple iMessage, etc.). The system may be configured to use the mobile contact information to transmit information about the form (e.g., form processing status) to the user. Alternatively or additionally, the system may be configured to use the mobile contact information in a process that obtains supplemental documentation via a camera in the user's mobile device.

In an embodiment, the system is configured to obtain supplemental documentation via webcam, file upload, mobile device camera, and/or in one or more other ways. To obtain supplemental documentation via a mobile device camera, the system may be configured to transmit a unique link to the user's mobile device. Upon a user selecting the link at the mobile device, the system may be configured to present an interface that guides the user through a process of capturing an image of the supplemental documentation using the mobile device's camera.

In an embodiment, the system is configured to transmit the form bundle, including structured and unstructured data, to a separate system that is controlled and operated by the healthcare organization. The healthcare organization may use information from the form bundle to trigger one or more automated processes. For example, the healthcare organization's receipt of the form bundle may trigger a process for initiating a new log entry and/or performing a records lookup via an application programming interface (API) of back-office software, such as release of information (ROI) software or electronic medical record (EMR) software.

FIG. 1 is a block diagram of an example of a system 100 according to an embodiment. In an embodiment, system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

In an embodiment, user interface 102 refers to hardware and/or software configured to facilitate communications between a user and form generation service 104. User interface 102 renders user interface elements and receives input via user interface elements. User interface 102 may be a graphical user interface (GUI), a command line interface (CLI), a haptic interface, a voice command interface, and/or any other kind of interface or combination thereof. Examples of user interface elements include checkboxes, radio buttons, dropdown lists, list boxes, buttons, toggles, text fields, date and time selectors, command lines, sliders, pages, and forms.

In an embodiment, different components of user interface 102 are specified in different languages. The behavior of user interface elements may be specified in a dynamic programming language, such as JavaScript. The content of user interface elements may be specified in a markup language, such as hypertext markup language (HTML) or Extensible Markup Language (XML) User Interface Language (XUL). The layout of user interface elements may be specified in a style sheet language, such as Cascading Style Sheets (CSS). Alternatively or additionally, aspects of user interface 102 may be specified in one or more other languages, such as Java, Python, Perl, C, C++, and/or any other language or combination thereof.

In an embodiment, user interface 102 renders user interface elements generated by a website plugin that is customized to a healthcare organization's specifications (e.g., corresponding to the healthcare organization's own form). The website plugin may be customized using a template that can be populated automatically. The website plugin may be hosted in a different location (e.g., separate cloud hosting) than a healthcare organization's own website. For example, form generation service 104 may include a software-as-a-service (SaaS) platform that serves the website plugin to the user interface 102. The website plugin may be embedded in the healthcare organization's website using a code snippet that loads the website plugin from the other hosting location. For example, the website plugin may be embedded in the healthcare organization's website using a snippet of JavaScript and hypertext markup language (HTML) that loads an inline frame (iframe) on the healthcare organization's website. Embedding a website plugin in the healthcare organization's website may allow for consistent branding for the healthcare organization, even if the user is interacting with user interface elements that are not hosted directly by the healthcare provider. The embedded website plugin may communicate securely with form generation service 104 to handle one or more form completion and submission operations described herein.

Alternatively, the user interface 102 may render user interface elements that are all hosted in the same location as the healthcare organization's website. For example, the hosting location may include one or more server-side scripts that generate one or more web pages for completing forms. The server-side script(s) may also be configured to communicate with form generation service 104 as needed to obtain, verify, and/or bundle form information as described herein.

In an embodiment, form generation service 104 refers to hardware and/or software configured to perform operations described herein for completing and submitting forms. Examples of operations for completing and submitting forms are described below. For example, form generation service 104 may be configured to perform operations for verifying a user's mobile contact information, processing images and/or other documents, populating and flattening forms, transmitting form bundles to recipients, generating alerts and/or notifications, integrating with back-office software, generating analytics, and/or other operations described herein.

In an embodiment, healthcare service 106 refers to hardware and/or software configured to perform operations described herein for receiving and processing a form bundle generated by form generation service 104. For example, healthcare service 106 may be configured to use information from a form bundle to perform an automated records lookup, using an application programming interface (API) of back-office service 108. In an embodiment, back-office service 108 refers to hardware and/or software configured to perform one or more back-office functions as described herein. In an embodiment, healthcare service 106 is under the control of a healthcare organization, separate from an entity that controls and/or operates form generation service 104.

In an embodiment, analytics interface 122 refers to hardware and/or software configured to facilitate communications between a user and form generation service 104. Specifically, analytics interface 122 is configured to present information about analytics 118 generated by form generation service 104. Analytics interface 122 may include one or more user interface features and/or components described above with respect to user interface 102.

In an embodiment, data repository 110 is any type of storage unit and/or device (e.g., a file system, database, collection of tables, or any other storage mechanism) for storing data. Data repository 110 may include multiple different storage units and/or devices. The multiple different storage units and/or devices may or may not be of the same type or located at the same physical site. Further, data repository 110 may be implemented or may execute on the same computing system as one or more other components of system 100. Alternatively or additionally, data repository 110 may be implemented or executed on a computing system separate from one or more other components of system 100. Data repository 110 may be logically integrated with one or more other components of system 100. Alternatively or additionally, data repository 110 may be communicatively coupled to one or more other components of system 100 via a direct connection or via a network. In FIG. 1, data repository 110 is illustrated as storing various kinds of information. Some or all of this information may be implemented and/or distributed across any of the components of system 100. However, this information is illustrated within the data repository 104 for purposes of clarity and explanation.

In an embodiment, data repository 110 uses 256-bit Advanced Encryption Standard (AES) to store data securely. Alternatively or additionally, data repository 110 may store data using 128-bit AES. Alternatively or additionally, data repository 110 may store data using another standard or combination thereof. Different sets of data may be stored using different standards. Some or all of data repository 110 may be configured to comply with HIPAA standards for storing data. In an embodiment, some data in data repository 110 is stored only temporarily, during the process of completing and submitting a form, and discarded when the process is complete. Other data may be stored longer-term, for example to be used for auditing and/or analytics as described herein.

In an embodiment, form 112 is an electronic form that generation service 104 populates with information provided by a user via user interface 102. Form 112 may be a portable document format (PDF) form, Microsoft Word® document, or another type of electronic form or combination thereof. Form 112 may include one or more fillable fields. Alternatively, form 112 may be a "flat" form.

In an embodiment, form template 114 maps structured data elements, which correspond to values of form fields and are produced as a result of user interactions with user interface 102, to locations in form 112. If form 112 is a flat form, form template 114 may map structured data elements to sets of coordinates (e.g., x, y coordinates) of where those fields exist on form 112. If form 112 has fillable fields, form template 113 may map a set of form field input names to the corresponding structured data elements. Alternatively or additionally, form generation service 104 may be configured to use natural language processing to match fillable form field input names with structured data elements, in which case form template 114 may be generated automatically.

In an embodiment, log data 116 refers to information that system 100 stores in connection with one or more uses of form generation service 104. Log data 116 may include some or all of the structured information and/or unstructured information provided by one or more users. Log data 116 may be associated with one or more forms that have been completed, submitted, and/or processed. Alternatively or additionally, log data 116 may be associated with one or more instances where a form was not completed and/or submitted. In an embodiment, some or all of log data 116 may be anonymized, to help protect user privacy and confidentiality.

In an embodiment, analytics 118 refers to analytic data based on one or more uses of form generation service 104. Analytics 118 may include aggregate analytics, based on aggregated log data 116 associated with multiple uses of form generation service 104.

In an embodiment, form bundle 120 refers to a combination of structured data (e.g., a populated instance of form 112) and unstructured data (e.g., supplemental documentation provided as described herein). Form bundle 120 maintains a logical connection between the structured data and the unstructured data, such that the two types of data can be stored and transmitted together. For example, form bundle 120 may be a PDF document with the unstructured data appended to the structured data. Form bundle 120 may take other forms.

In an embodiment, one or more components of system 100 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

3. Completing and Submitting a Form

Figure 2A:
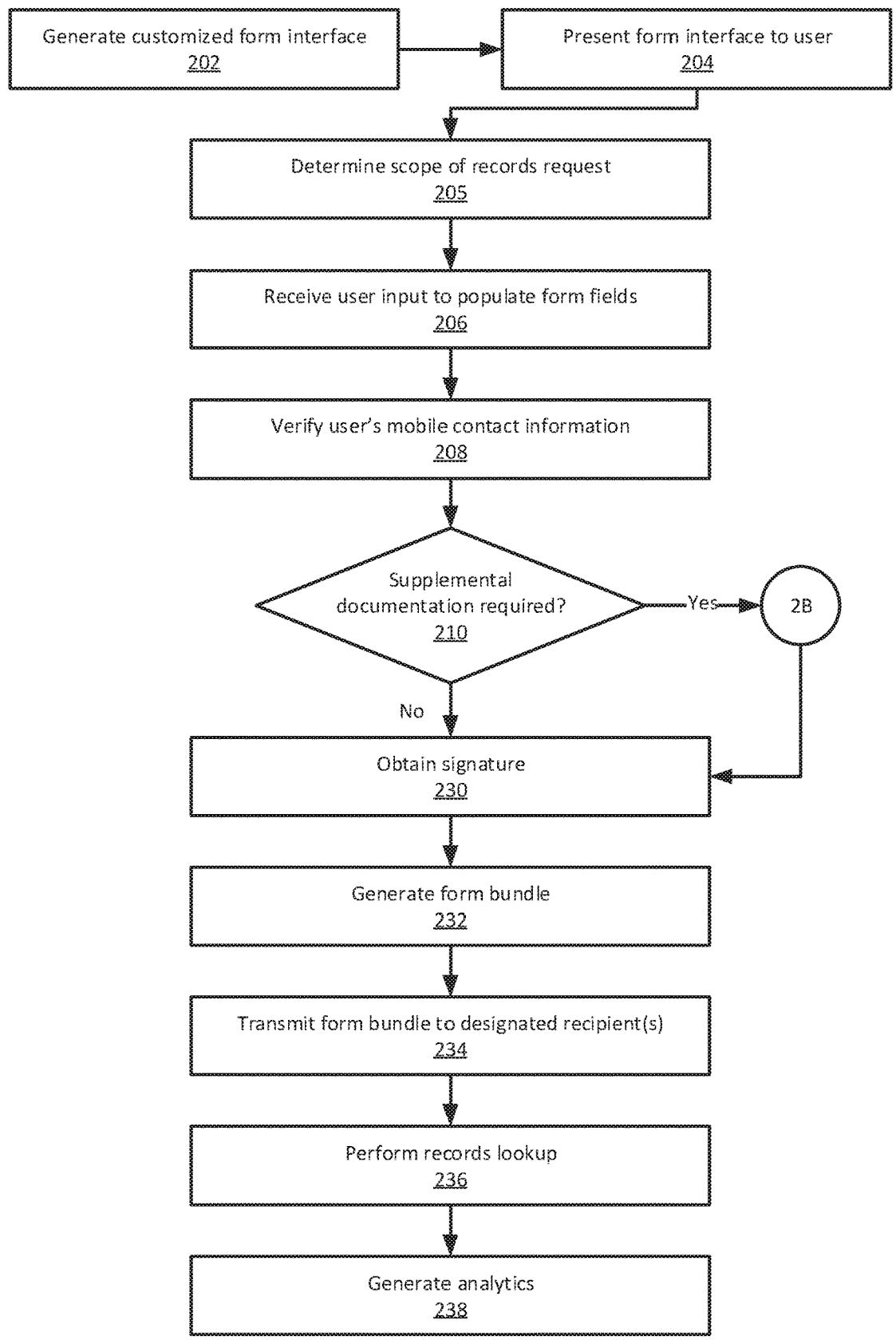
FIGS. 2A-2B are a flow diagram of an example of operations for completing and submitting a form according to an embodiment.
Figure 2B:
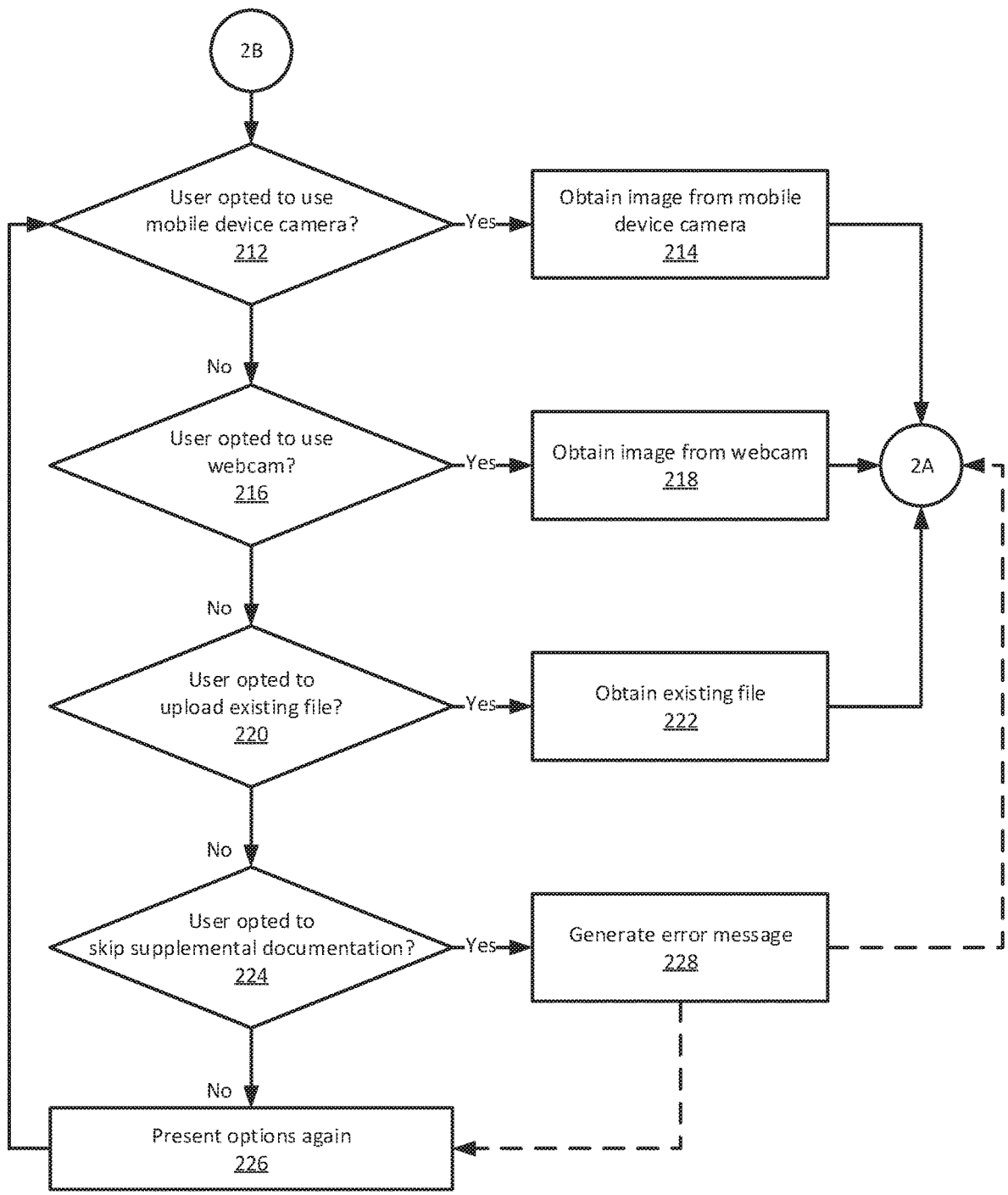

FIGS. 2A-2B are a flow diagram of an example of operations for completing and submitting a form according to an embodiment. One or more operations illustrated in FIGS. 2A-2B may be modified, rearranged, or omitted all together. Accordingly, the particular sequence of operations illustrated in FIGS. 2A-2B should not be construed as limiting the scope of one or more embodiments.

In an embodiment, a system (e.g., one or more components of system 100 illustrated in FIG. 1) generates a customized form interface (202). Specifically, the system may generate the customized form interface according to specifications provided by a healthcare organizations. The system may generate the customized form interface using a form template that indicates, for the particular form in question, which form fields are to be completed.

In an embodiment, the system presents a form interface to a user (Operation 204). The form interface may be a step-by-step 'wizard' that guides the user through a process of completing the form. The form interface may offer detailed descriptions about the information being requested at each step, when such descriptions are needed and/or available. In an embodiment, the system obtains the detailed descriptions from a library of descriptions that can be modified, configured, or customized for each healthcare organization. The specific information requested depends on which form is being completed and may differ between health care organizations.

In an embodiment, the form is a medical records release form, the system determines the scope of the records request (Operation 205). One or more of the form fields may require the user to select from a list of possible reasons for the request. For example, possible reasons may include one or more of a job, school, a legal issue, an insurance application, continued care, patient request, undisclosed, etc. Based on the reason(s) that that the user selects, the system may recommend and/or preselect a type of records to be released. For example, if the user selects "job" as the reason, the system may preselect "immunizations" as a record type to be released. If the user selects "continued care" as the reason, the system may select "abstract" as a record type to be released. The recommended records may correspond to the smallest set of records that typically satisfy the kind of request indicated. In this manner, the system may help reduce the volume of records being requested, which may reduce the user's cost of making the request (e.g., if the cost of the request is based on number of records provided and/or the number of pages thereof). For example, an "abstract" of a medical history is typically considerably smaller than a full set of treatment records. In addition, a smaller set of records may be more manageable the healthcare provider (e.g., the healthcare provider may be able to more readily locate and/or assemble a smaller set of records) and may therefore help streamline the records' intended use. The system may prompt the user to accept the recommendation or request a different scope of medical records to release.

In an embodiment, as part of determining the scope of the records request, the system may provide the user an option to select whether to release "sensitive" information (e.g., mental health information, disease status, etc.) that may not be pertinent to the purpose of the records request. Depending, for example, on organizational preference, disclosing sensitive information may be opt-in, opt-out, or non-optional. Alternatively or additionally, the system may provide the user an option to indicate an expiration date for the release authorization (e.g., a specific date or a certain amount of time after the release). Depending on organizational preference, users may not have the option to select an expiration date; a default expiration date may be used.

In an embodiment, the system receives user input to populate one or more form fields (Operation 206). The user input may include information (unless the information has already been provided) such as the requestor's name, a scope of release of medical records (i.e., a complete release or a release that is limited to one or more of types of records, such as mental health records, communicable diseases, alcohol/drug abuse treatment records, genetic, information, etc.), a medium of disclosure being authorized (e.g., electronic and/or hard copy), a reason for requesting a release of medical records, who is authorized to receive the medical records, and/or other information depending on the specific form being completed.

In an embodiment, one or more form fields ask the user to indicate a deadline for the request, i.e., when the request needs to be completed. For example, if the user is requesting a release of medical records as part of a lawsuit, the user may be subject to a discovery deadline. If the user specifies a deadline, the system may send timely notification alerts to the healthcare organization. Such alerts may help the healthcare organization prioritize the request appropriately and help ensure that the request is completed before the deadline.

In an embodiment, the system verifies the user's mobile contact information (Operation 208). Mobile contact information may include a mobile phone number, email address, instant messaging handle, and/or another type of mobile contact information. Verifying a user's mobile contact information confirms that the user is reachable on a mobile device using the contact information provided. The system may verify the user's mobile contact information in many different ways. In an embodiment, responsive to the user providing mobile contact information, the system uses transmits a unique code to the mobile device. For example, if the mobile contact information is a phone number, the system may transmit a simple messaging system (SMS) message to that phone number. To verify the mobile contact information, the user is required to enter the unique code into the form interface.

In an embodiment, the system uses mobile contact information to help the healthcare organization match the user with existing information (e.g., when looking up patient records). Alternatively or additionally, the system may use mobile contact information to send updates (e.g., SMS messages) to the user regarding the status of the healthcare organization's processing of the form (e.g., "Reviewing Request," "Records Located," "Records Sent to Destination," etc.). The system may transmit such messages responsive to detecting triggers (e.g., changes in status fields) in back-office software. Alternatively or additionally, the system may use mobile contact information in a process for obtaining supplemental documentation from a mobile device camera, as described herein. The system may use mobile contact information for many different purposes.

In an embodiment, the system determines whether supplemental documentation is required (Operation 210). For some forms, supplemental documentation may always be required. For other forms, supplemental documentation may be required only under certain conditions, which may be based on user input. For example, if a user is requesting the release of medical records on behalf of somebody else, the system may determine that documentation of a medical power of attorney is required. For some forms, some supplemental documentation may always be required (e.g., photo identification) and other supplemental documentation (e.g., medical power of attorney) may be conditionally required.

In an embodiment, multiple forms of supplemental documentation are permitted to satisfy a particular requirement. For example, for a form that requires photo identification, the requirement may be satisfied by a driver's license, government identification (e.g., passport), and/or another form of photo identification. When multiple forms of supplemental documentation are permitted, the system may request user input indicating which form of supplemental documentation is being provided.

In an embodiment, when supplemental documentation is required, the form interface guides the user through a process of providing the supplemental documentation. For example, the form interface may present an additional screen (e.g., webpage or application screen) with user interface controls for providing supplemental documentation. The system may be configured to obtain supplemental documentation in many different ways. In an embodiment, the system presents multiple options to the user, and the user selects one of the available options. Alternatively, the system may default to a particular option (e.g., webcam) and make another option available only if the default option fails (e.g., if a webcam is not detected and/or authorized).

In an embodiment, the system determines whether the user has opted to use a mobile device camera to provide the supplemental documentation (Operation 212). If the user has opted to use a mobile device camera, then the system obtains an image from the mobile device camera (Operation 214). Before obtaining the image, the system may use mobile contact information to direct the user to an image capture interface on the user's mobile device. The mobile contact information may be mobile contact information that was verified as described above. If mobile contact information has already been verified, the system may provide the user with the option of using the same mobile device for image capture. Alternatively or additionally, the system may allow the user to verify different mobile contact information. Some embodiments only allow the user to verify one set of mobile contact information. If mobile contact information has not already been verified, or if the user wishes to verify different mobile contact information (if permitted), then the system may guide the user through the verification process.

In an embodiment, the system generates a unique link and transmits the link to the user, at the verified mobile contact information (e.g., an SMS message to a verified phone number). Responsive to the user selecting the link, the system presents an interface for capturing the image. Specifically, the user may hold or place the supplemental documentation in front of the mobile device camera. The system may facilitate image capture by presenting, in the user interface, a view of what the mobile device cameras 'sees,' to help the user ensure that the entire document is captured and in focus. The system may send a signal to the mobile device camera to capture the image, responsive to user input indicating that the supplemental documentation is in place and/or responsive to detecting that the supplemental documentation is properly situated in the mobile device camera's field of view. The system receives and stores the image captured by the mobile device camera.

In an embodiment, a user initially accesses the form interface on a device other than the mobile device used to capture the image of the supplemental documentation. After the user provides supplemental documentation via the mobile device camera, the user may be able to continue completing the form on the mobile device. The system may populate the interface on the mobile device with information that was previously provided and/or generated using the other device. The interface on the mobile device may thus allow the user to finish the process of completing and submitting the form on the mobile device. In addition, the user may be able to navigate backwards in the process, to revise information that was previously provided on the other device. Alternatively, after the user provides supplemental documentation via the mobile device camera, the system may update the interface on the original device and allow the user to continue the process on that device.

In an embodiment, the system determines whether the user has opted to use a webcam to provide the supplemental documentation (Operation 216). The system may request the user's permission to access the webcam. For example, the user may be required to authorize access to the webcam via a web browser. If the user has opted to use a webcam, then the system obtains an image from the webcam (Operation 218). Specifically, the user may hold or place the supplemental documentation in front of the webcam. The system may facilitate image capture by presenting, in the user interface, a view of what the webcam 'sees,' to help the user ensure that the entire document is captured and in focus. The system may send a signal to the webcam to capture the image, responsive to user input indicating that the supplemental documentation is in place and/or responsive to detecting that the supplemental documentation is properly situated in the webcam's field of view. The system receives and stores the image captured by the webcam.

In an embodiment, if the system does not detect a webcam on the user's device and/or the user does not grant permission to access the webcam, the system may present one or more other options for providing the supplemental documentation.

In an embodiment, the system determines whether the user has opted to upload an existing file that includes the supplemental documentation (Operation 220). Specifically, the user may already have the supplemental documentation stored on their device, for example as a scan of a driver's license or other supplemental documentation. If the user has opted to upload an existing document, then the system obtains the existing file (Operation 222). To obtain the existing file, the system may present user interface controls that allow the user to locate the existing file and upload the file to the system.

In an embodiment, the system determines whether the user has opted to skip supplying the requested supplemental documentation (Operation 224). Determining that the user has opted to skip supplying the supplemental documentation may be based on an explicit user command (e.g., selecting a user input control to "skip this step" or another similar kind of input). Alternatively, determining that the user has opted to skip supplying the supplemental documentation may be based on the user having declined the available options (e.g., mobile device camera, webcam, and/or file upload, depending on the available options). The system may ask the user to confirm that they intend to skip supplying the supplemental documentation. If the user indicates that they do wish to supply supplemental documentation, then the system may present the available options again (Operation 226), either as a list or one-by-one. The user may then have another opportunity to supply the supplemental documentation in one or more ways described herein.

In an embodiment, if the user does not select from any of the available options for providing the supplemental documentation (i.e., one of the options described above or another option that supplies a digital representation of the supplemental documentation), and/or explicitly skips providing supplemental documentation, the system may be unable to proceed with submitting the form. The system may generate an error message (Operation 228), but proceed with submitting the form without the supplemental documentation. The system may warn the user (e.g., via an error message in Operation 228) that the form will be incomplete as submitted. The warning may indicate that the lack of supplemental documentation could delay processing of the form. The user may be required to provide the supplemental documentation at a later time. Alternatively, if the user does not provide the requested supplemental documentation, the system may stop the process of preparing and submitting the form. The warning may provide the user with the option to revisit the options for supplying supplemental documentation (Operation 226).

Returning to FIG. 2A, in an embodiment, when the user has completed the required form fields and provided the required supplemental documentation (if any), the system obtains a signature (Operation 230). Specifically, the system obtains an electronic signature in a format that the healthcare organization considers acceptable in lieu of a physical signature. The user may draw an electronic signature using their finger (e.g., on a touchscreen or trackpad) or a mouse. Alternatively, the user may type their signature into a textbox. Alternatively, the user may supply a digital certificate or other unique token to be treated as an electronic signature. Many different techniques for obtaining electronic signatures may be used.

In an embodiment, at some point in the process described herein, the system may provide the user with an estimate of the cost to submit the form. For example, the cost may be based on what kind of information is requested to be released, an estimate of the number of pages of records, etc. The system may obtain payment information, such as a credit card number, electronic payment system (e.g., PayPal, Venmo, Zelle, Google Pay, Apple Pay, etc.) account information, bank account and routing number, and/or another kind of payment information. The system may require full payment using a single payment method. Alternatively, the user may be able to split payment across two or more payment methods. Signing the form may also serve as pre-authorization to charge the estimated costs to the payment method(s) provided. For a credit card pre-authorization, the system may place an authorization hold on the credit card account for the estimated amount, to be settled once the final amount is known. The payment pre-authorization may require a separate signature or may rely on the same signature(s) also used elsewhere.

In an embodiment, the system generates a form bundle (Operation 232). The system may generate the form bundle before or after obtaining the signature. For example, the system may generate the form bundle after the user has signed and opted to submit the form (e.g., by clicking or tapping a "submit" button). The form bundle may a PDF file or other type of data. If the user is accessing the form interface on a smartphone or older browser, the form bundle may be converted to one or more image files for increased cross-platform compatibility. In an embodiment, the form bundle includes a populated form that is bundled with one or more of: supplemental documentation; an audit trail page; the user's verified mobile contact information; and/or other information bundled with the populated form.

In an embodiment, to populate the form, the system populates form fields with corresponding structured data received and/or generated in response to user input to the form interface. The system may store multiple forms and select which form to populate based on a form identifier (e.g., an identifier that is transmitted by the form interface and/or stored as part of a user session). The system may populate the form using a form template that maps structured data to locations and/or form field names, as described above. In an embodiment, the system 'flattens' the populated form to remove layering information. In the case of a fillable form (e.g., a fillable PDF form), flattening the form maintains integrity of the form by preventing fillable form fields from being further edited.

In an embodiment, the system appends supplemental documentation, obtained as described above, to the form. As used herein, the term 'append' should not be construed as implying a particular page ordering. The supplemental documentation may be appended before the page(s) that make up the form, after the page(s) that make up the form, or between two pages of the form. Different types of supplemental documentation may be appended at different locations.

In an embodiment, the system appends an audit trail page to the form. The audit trail form may be included in the form bundle that is transmitted to the healthcare organization, but omitted from the form bundle that is transmitted to the requestor. The audit trail page may include any kind of information about the provenance of the form bundle, such as the user's Internet Protocol (IP) address and/or date and timestamps of when the form bundle was viewed, signed, and/or completed by the user.

In an embodiment, the system appends a page with the user's verified mobile contact information to the form. Appending the user's verified mobile contact information may help the healthcare organization match the form bundle with existing records, such as patient records being requested.

In an embodiment, after completing and submitting a form as described herein, a user may use the same form interface to repeat the process. For example, the user may use the form interface to request another release of medical records, to a different entity and/or for a different reason. Responsive to user input to repeat the process, the system may prepopulate some information that was previously provided (e.g., name, date of birth, address, etc.). Alternatively or additionally, the system may clear some information that was previously provided (e.g., delivery destination and record types being requested). In an embodiment, prepopulating the form interface for a subsequent request makes the process of submitting multiple requests faster and reduces opportunities for user errors.

In an embodiment, after completing and submitting a form as described herein, the system presents the user with user interface controls for providing feedback on the experience of using the form interface. The system may store the feedback for future reference, e.g., for quality control. Alternatively or additionally, the system may aggregate the feedback with other user feedback, to be used for analytics. In an embodiment, the user is asked to provide feedback that can be incorporated into a provider's Hospital Consumer Assessment of Healthcare Providers and Systems (HCAHPS) survey results.

In an embodiment, the system transmits the form bundle to one or more designated recipients (Operation 234). The recipients may include one or more healthcare organizations (e.g., via a healthcare service as described with respect to FIG. 1), the requestor, and/or another person or entity who the requestor has authorized to receive the form bundle.

In an embodiment, before transmitting the form bundle, the system packages the form bundle in a data structure expected by the recipient. For example, the system may package the form bundle in an extensible markup language (XML) data structure. The system may encode the form bundle as part of the data structure. For example, the system may encode a PDF in an XML element as a base64 encoded string. In an embodiment, the system also stores some or all of the structured data from the form within separate elements in the data structure. For example, the system may store structured data as XML elements, according to an XML schema that maps form fields to corresponding XML elements. The XML schema may be consumable by a back-office service (e.g., release of information (ROI) software) without requiring the back-office service to parse the data from the form bundle itself.

In an embodiment, the system transmits a form bundle electronically to a healthcare service, using a transmission method already supported by the healthcare service. For example, the healthcare service may be configured to receive data via Secure File Transfer Protocol (SFTP) and/or File Transfer Protocol Secure (FTPS), such that the healthcare service does not require any modification of existing technology to receive the form bundle. Thus, one or more embodiments allow for the completion and submission of forms to healthcare organizations, without disrupting existing workflow processes.

In addition to transmitting the form bundle to a healthcare organization, the system may transmit the form bundle to the requestor. For example, when somebody requests a release of medical records, HIPAA regulations require healthcare organizations to provide the requestor with a copy of the completed form if asked. The system may have obtained consent to do so (e.g., when prompting the user for an email address, or at another point in the form completion process), and may send a copy of the completed form to the requestor (e.g., at the email address provided) after submission. For the copy of the form transmitted to the requestor, the system may modify one or more portions of the form bundle accordingly. For example, the system may alter "destination" and "delivery" portions of the completed form to reflect the user's information instead of the healthcare organization. Thus, the system may both transmit the completed form to the healthcare organization and supply a copy to the requestor, in a single process without requiring the requestor to make a new request for their own copy. The system may transmit the form bundle to multiple recipients in response to a single user input requesting submission of the form. In an embodiment, whereas information transmitted to a healthcare organization uses secure data transfer techniques, the requestor may have consented to receiving a copy of the form bundle via a less secure channel, such as unencrypted email.

In an embodiment, the system performs a records lookup, using information from the form bundle (Operation 236). In an embodiment, the lookup is an automated process using information from the form bundle. Alternatively, the lookup may be based on information in a data structure (e.g., XML) in which the form bundle is packaged, as described above. The records lookup may be performed by a healthcare service, by accessing an API of a back-office service (e.g., electronic medical record (EMR) software). The back-office service may return any records identified in the lookup to the healthcare service, without requiring a human operator to manually review the form bundle and manually enter information to perform the lookup.

In an embodiment, the system generates analytics associated with one or more uses of the form interface (Operation 238). Specifically, the analytics may be based on log data (which may include structured information and/or unstructured information provided by one or more users) for one or more forms that have been completed, submitted, and/or processed. Alternatively or additionally, the log data may include information about uses of the form interface where the form was not completed and/or submitted. The analytics may be aggregate analytics, based on aggregated log data associated with multiple uses of the form interface. For example, data from multiple uses of the form interface may be piped into a database, spreadsheet (e.g., a Google Sheet), and/or another kind of records storage or combination thereof. A dashboard interface may allow an administrator to visualize the aggregate data in various ways, to obtain insights into how the form is being used and/or types of data being provided. For example, the analytics may indicate (as absolute numbers, percentages, trend lines, etc.) which type(s) of devices are being used to submit forms, which image capture options (e.g., mobile device, webcam, and/or file upload) are being used, user satisfaction and/or comments provided in feedback, and/or any other kind of information discernable from the aggregate data. Analytics may be helpful to healthcare organizations in predicting staffing needs, for example.

In one or more embodiments, techniques described herein may be applied to forms other than those submitted to healthcare providers. For example, techniques described herein may be used to bundle unstructured supplemental documentation with one or more of: insurance and disability claims; government benefits applications and registration forms; education-related forms and applications; military-related forms and applications; housing applications; financial forms; and/or employment-related forms (e.g., job applications, employee onboarding, etc.). In general, techniques described herein may be used to bundle structured form data with unstructured supplemental documentation in a variety of industries, for a variety of purposes.

4. Detailed Examples

Detailed examples are described below for purposes of clarity. Components and/or operations described below should be understood as examples that may not be applicable to one or more embodiments. Accordingly, components and/or operations described below should not be construed as limiting the scope of one or more embodiments. In the following examples, various information (e.g., names and contact information) has been anonymized.

FIGS. 3A-3MM illustrate an example according to an embodiment. Specifically, FIGS. 3A-3MM illustrate an example of a user requesting a medical records release from a healthcare organization, according to an embodiment. In this example, as described in further detail below, the user begins the process on a personal computer (PC). As used herein, the term "PC" may refer to any kind of personal computer, including but not limited to: MacOS devices, Microsoft Windows devices, Chrome OS devices, Linux devices, etc. The workflow transfers to the user's mobile device to obtain supplemental documentation, and the user completes the process using the mobile device. In other examples, a user may complete the entire process, from start to finish, using a mobile device.

Figure 3B:
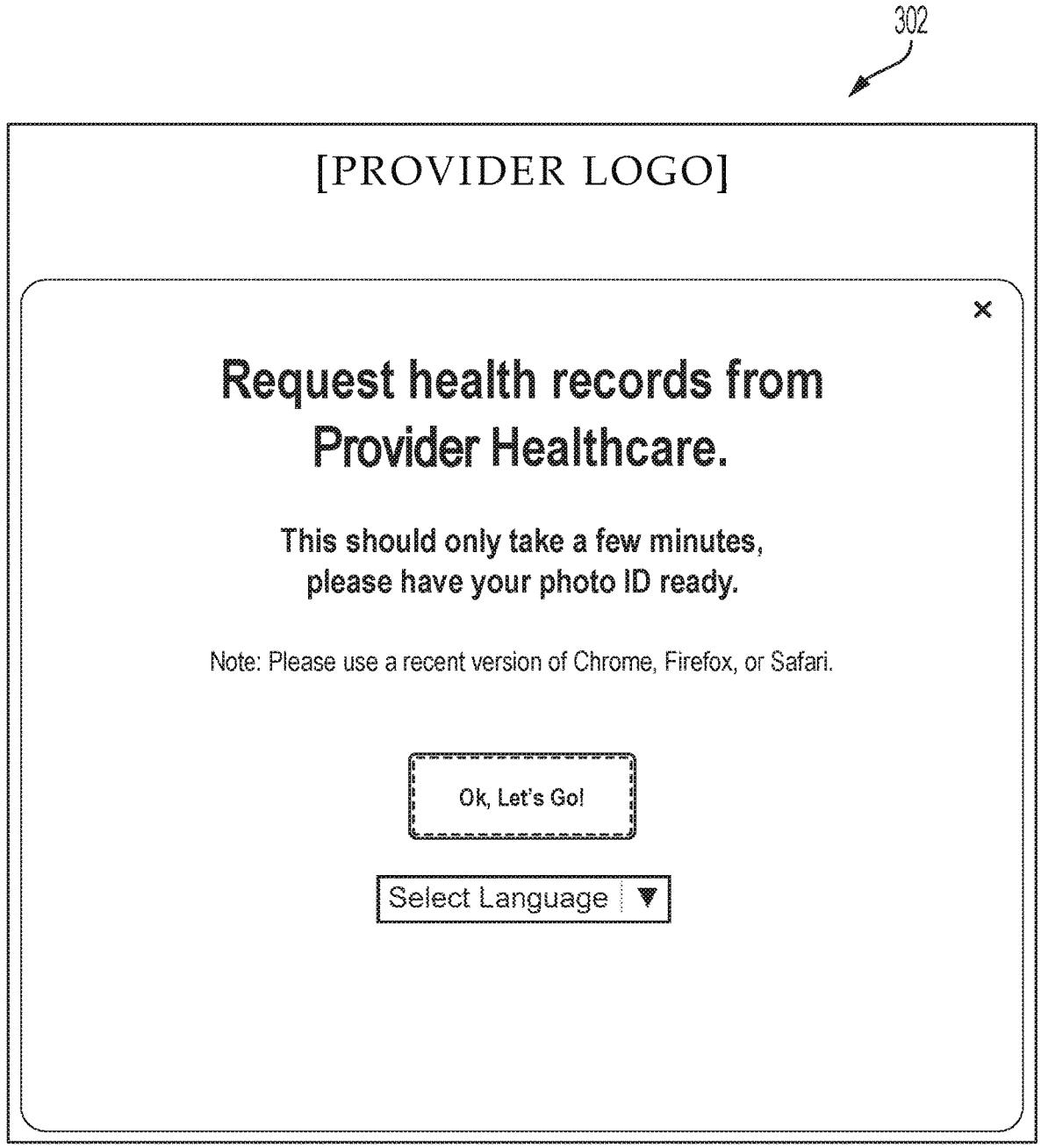
FIGS. 3A-3MM illustrate examples according to an embodiment.
Figure 3C:
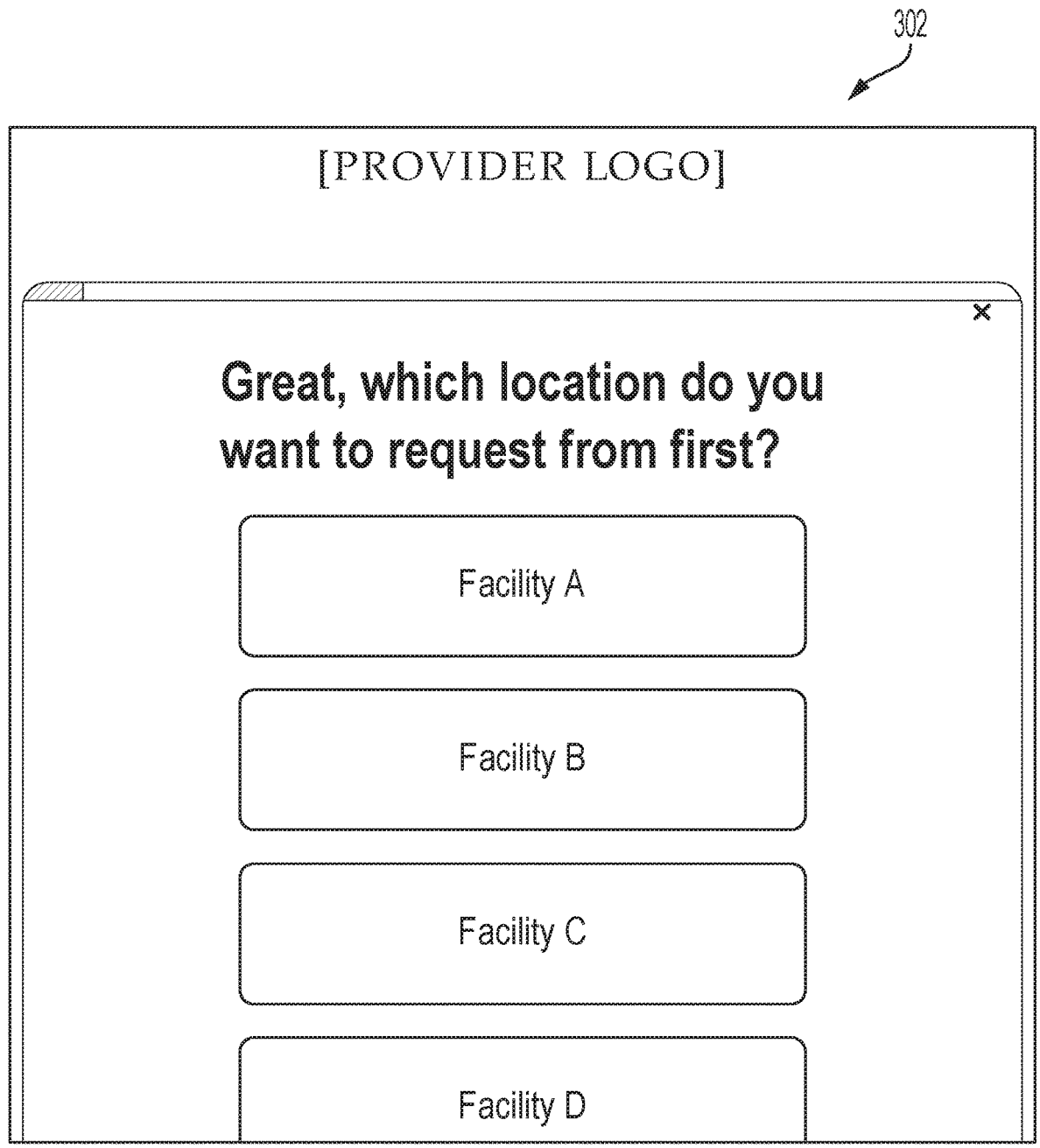
Figure 3D:
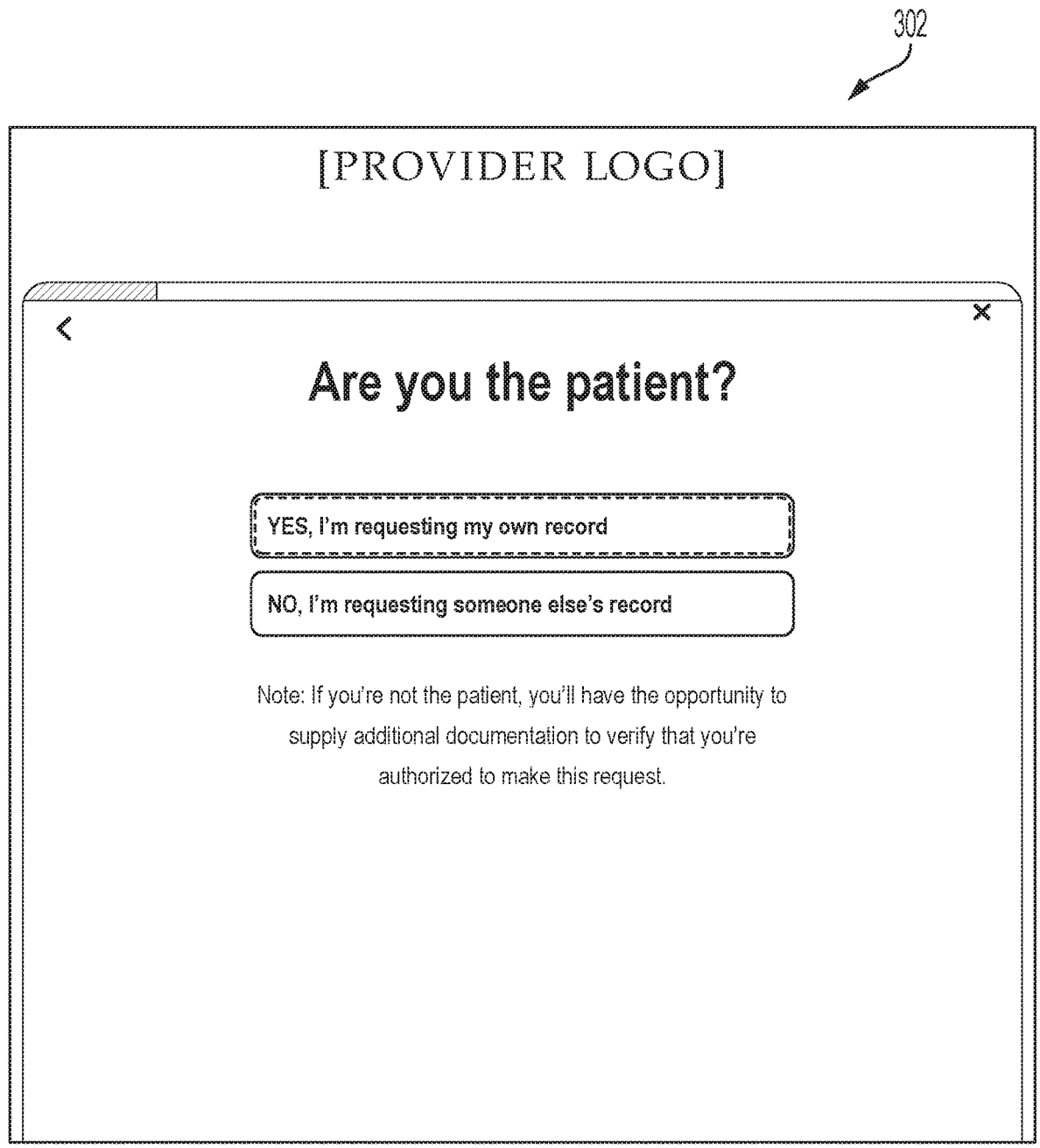
Figure 3E:
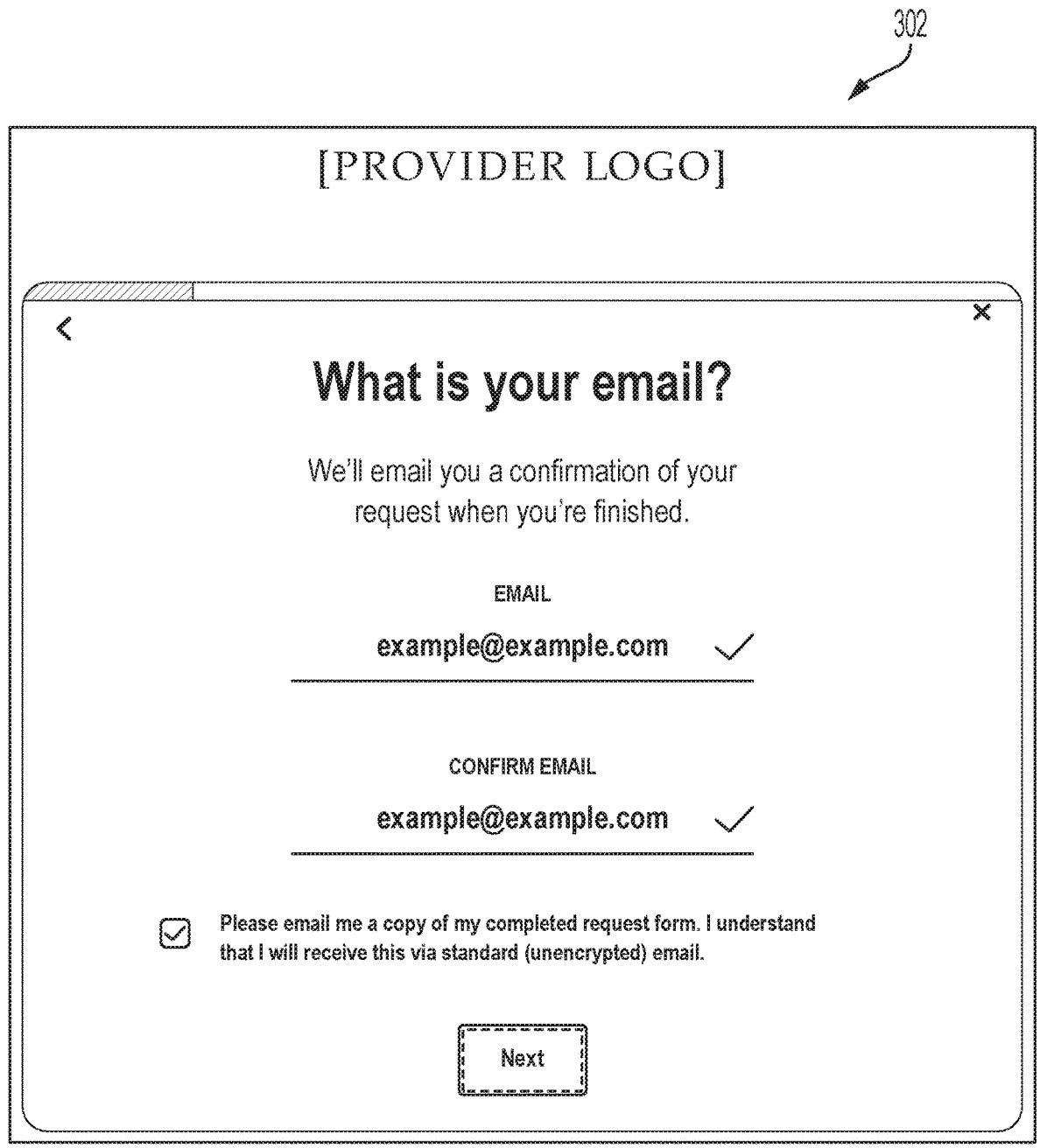
Figure 3G:
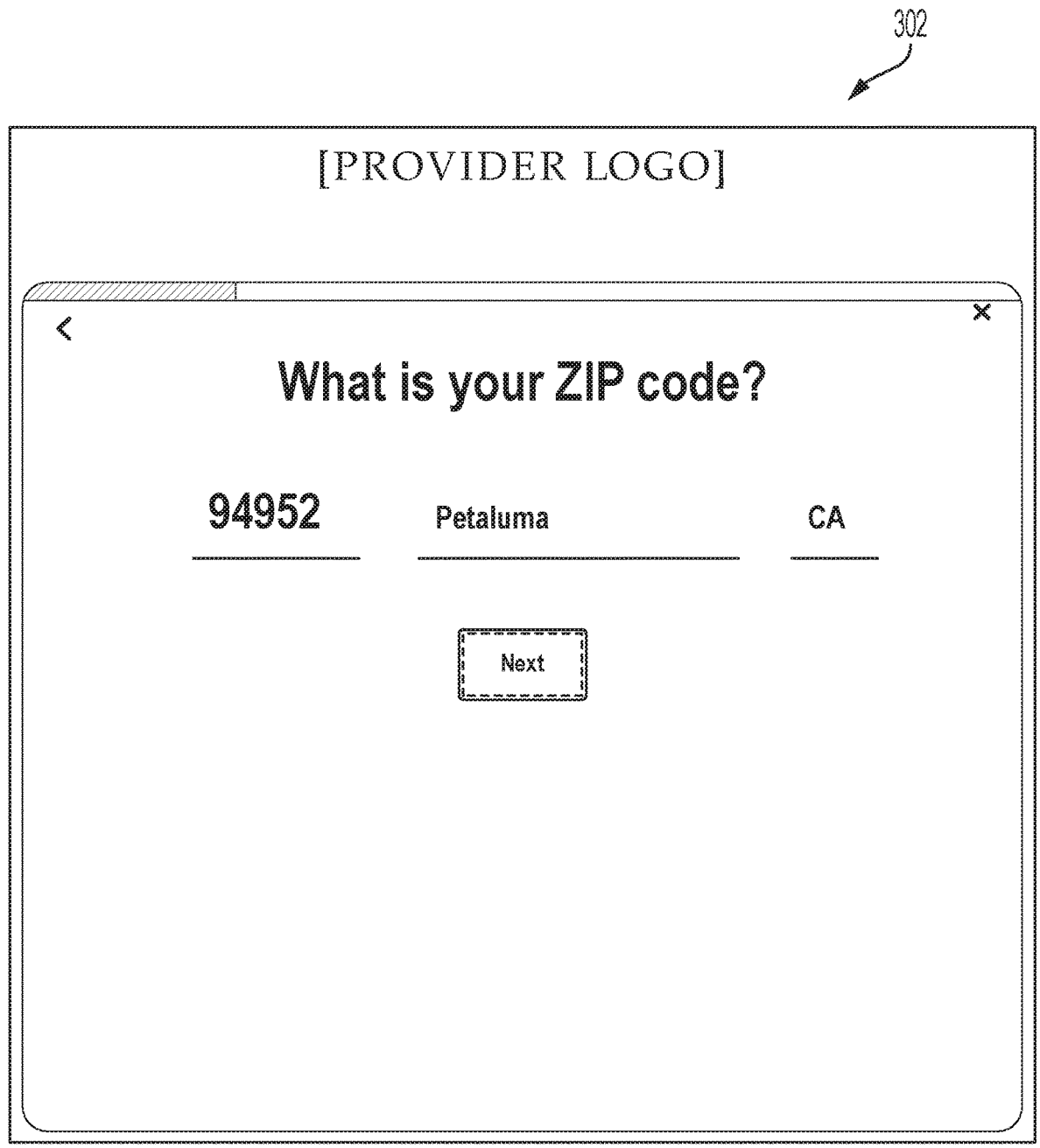
Figure 3H:
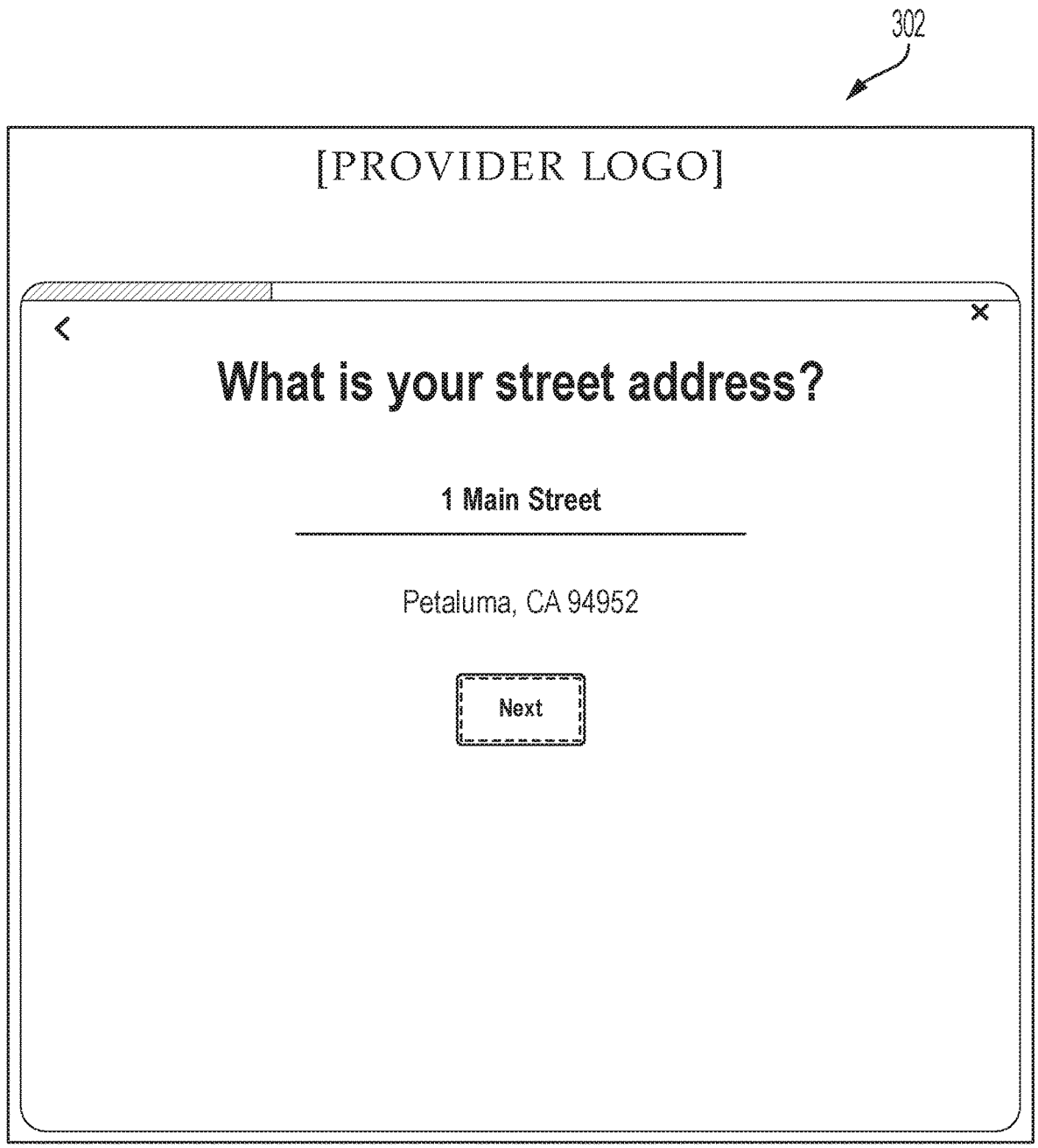
Figure 3I:
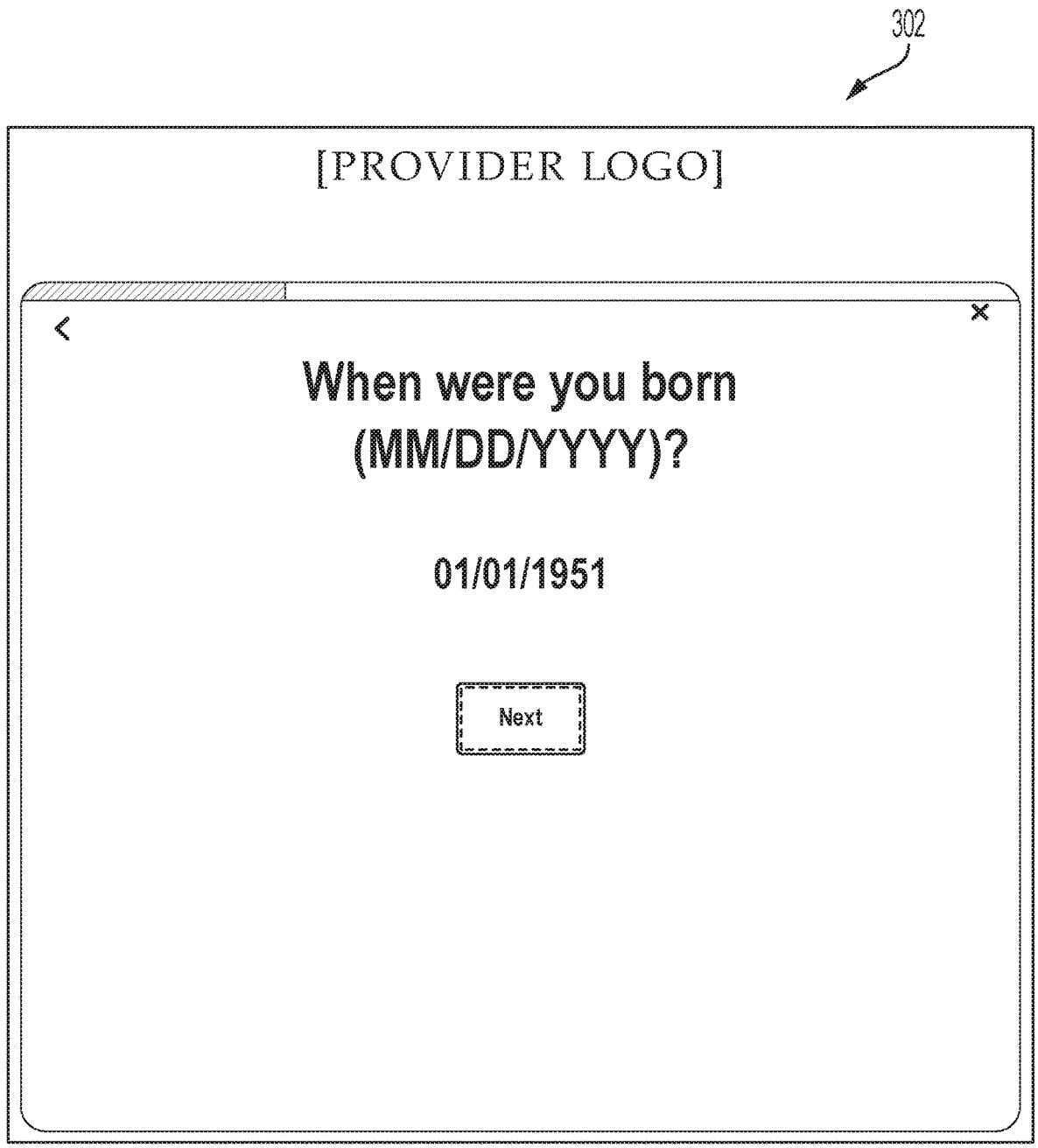
Figure 3J:
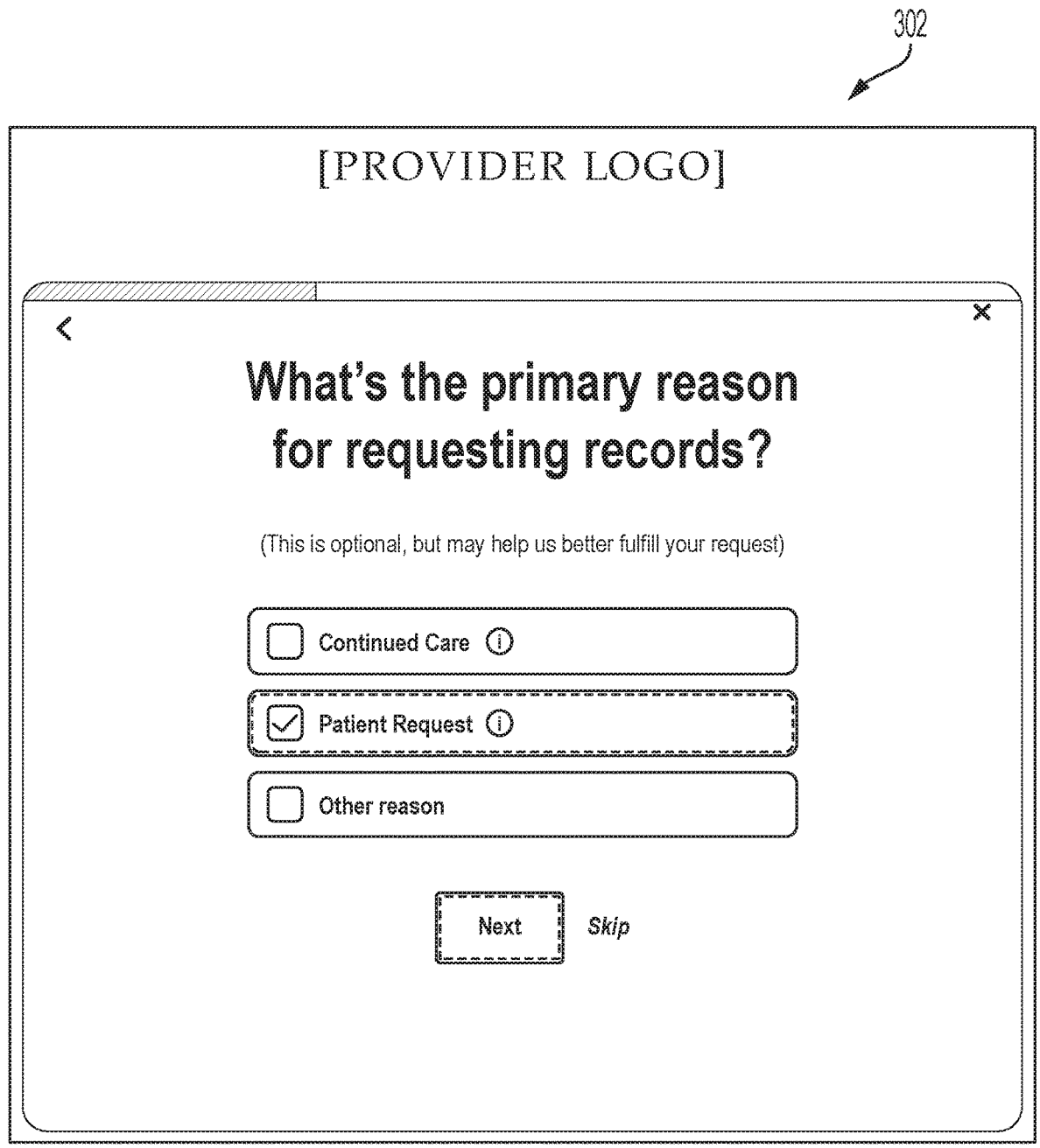
Figure 3K:
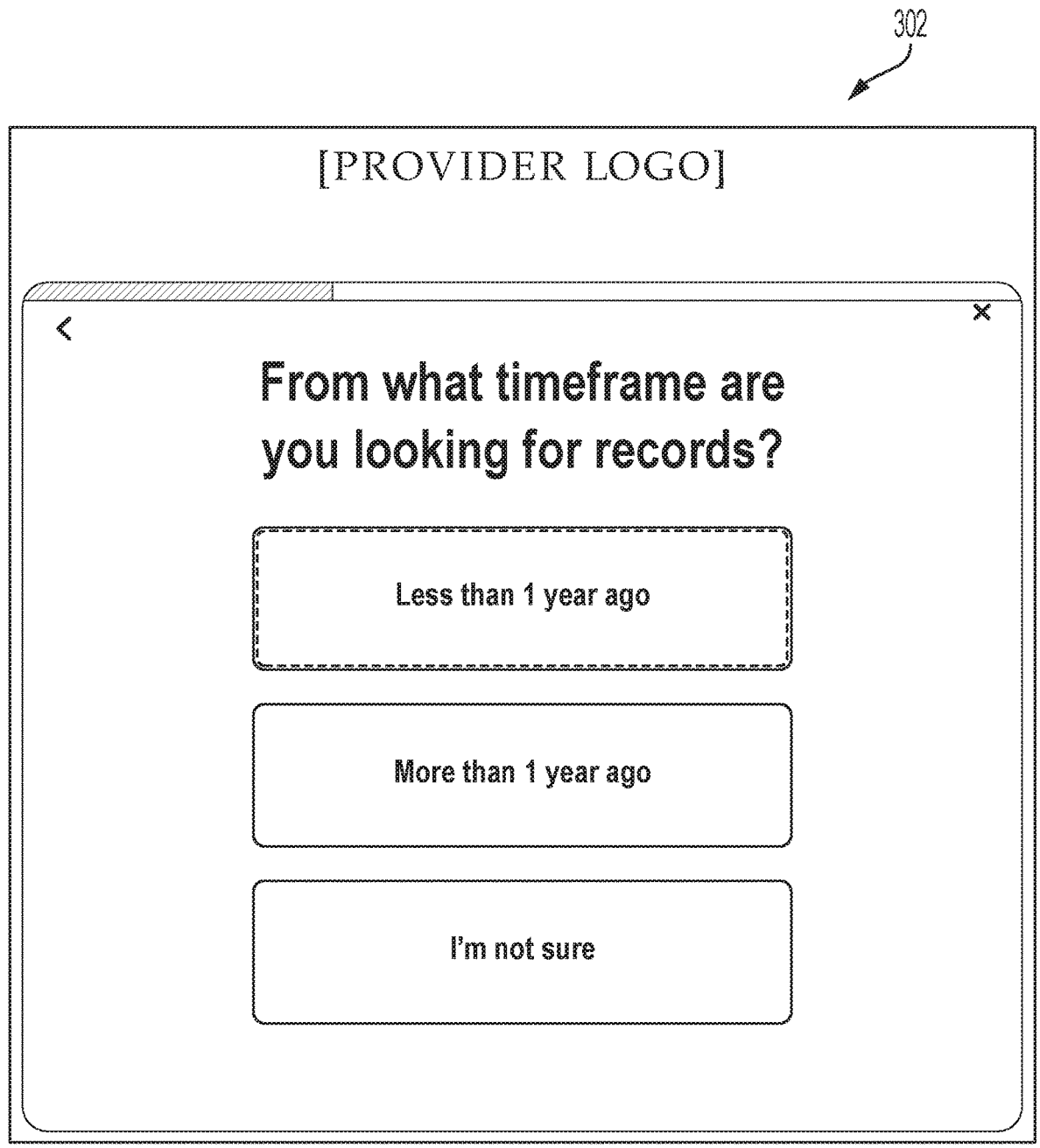
Figure 3L:
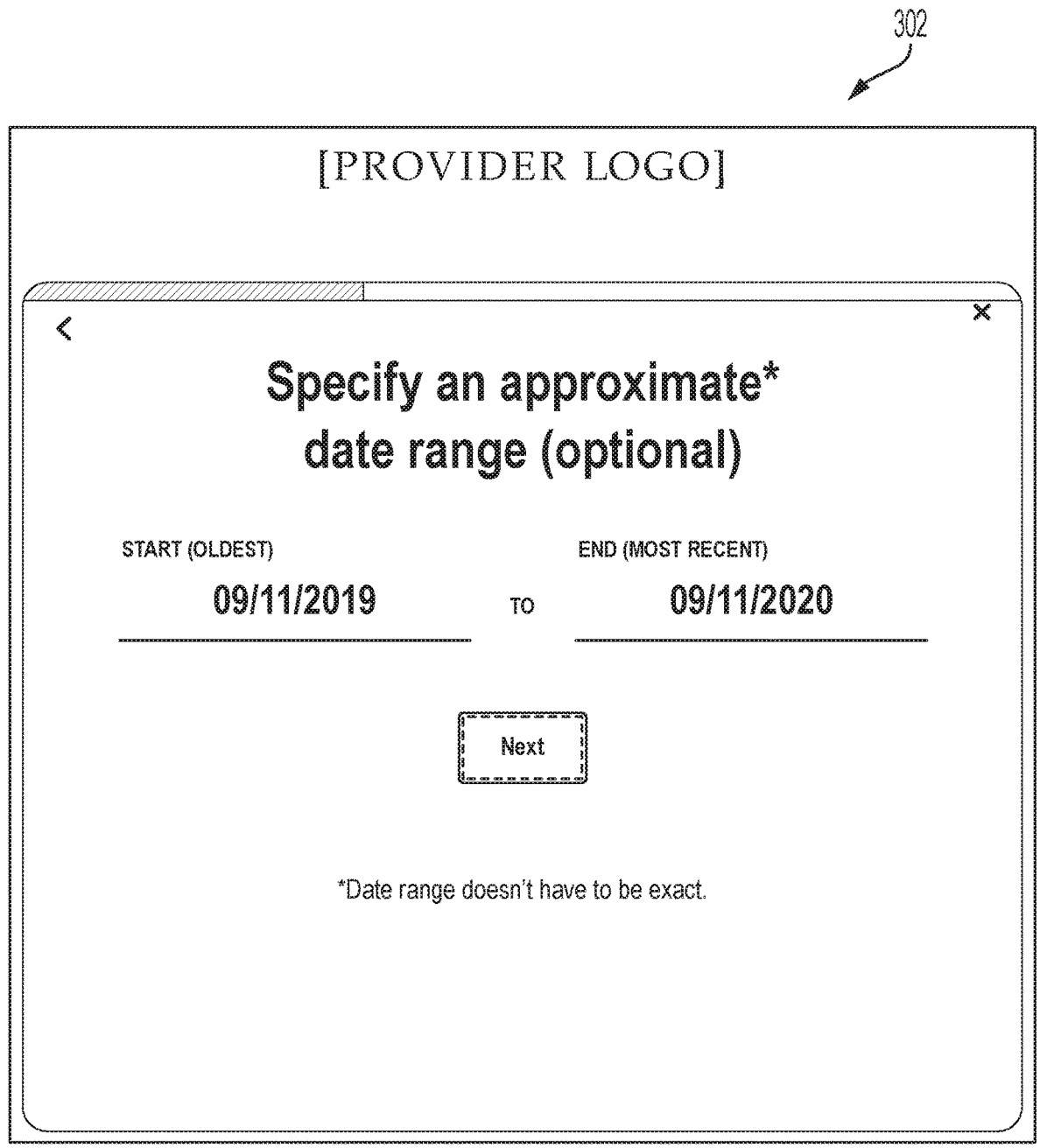
Figure 3M:
Figure 3N:
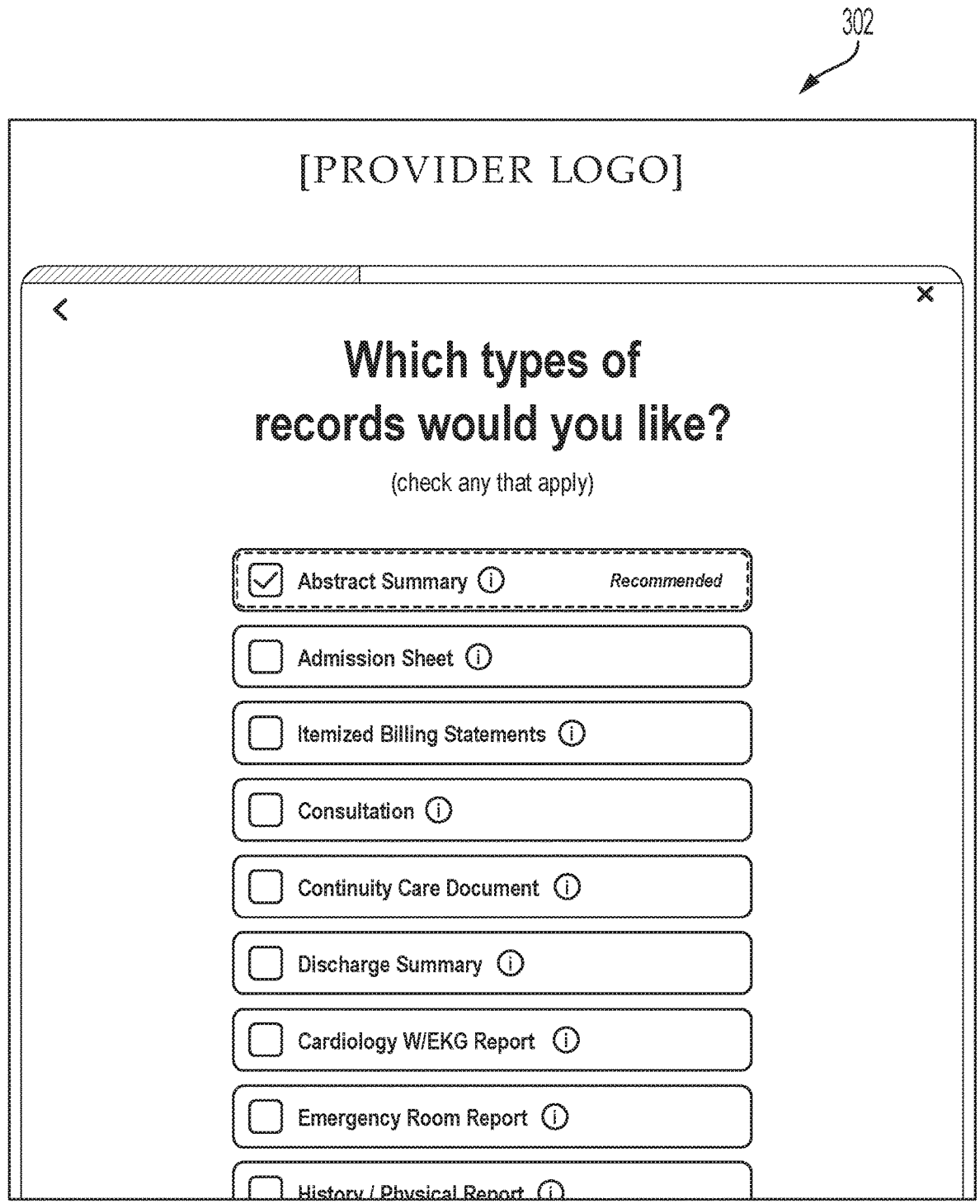
Figure 30:
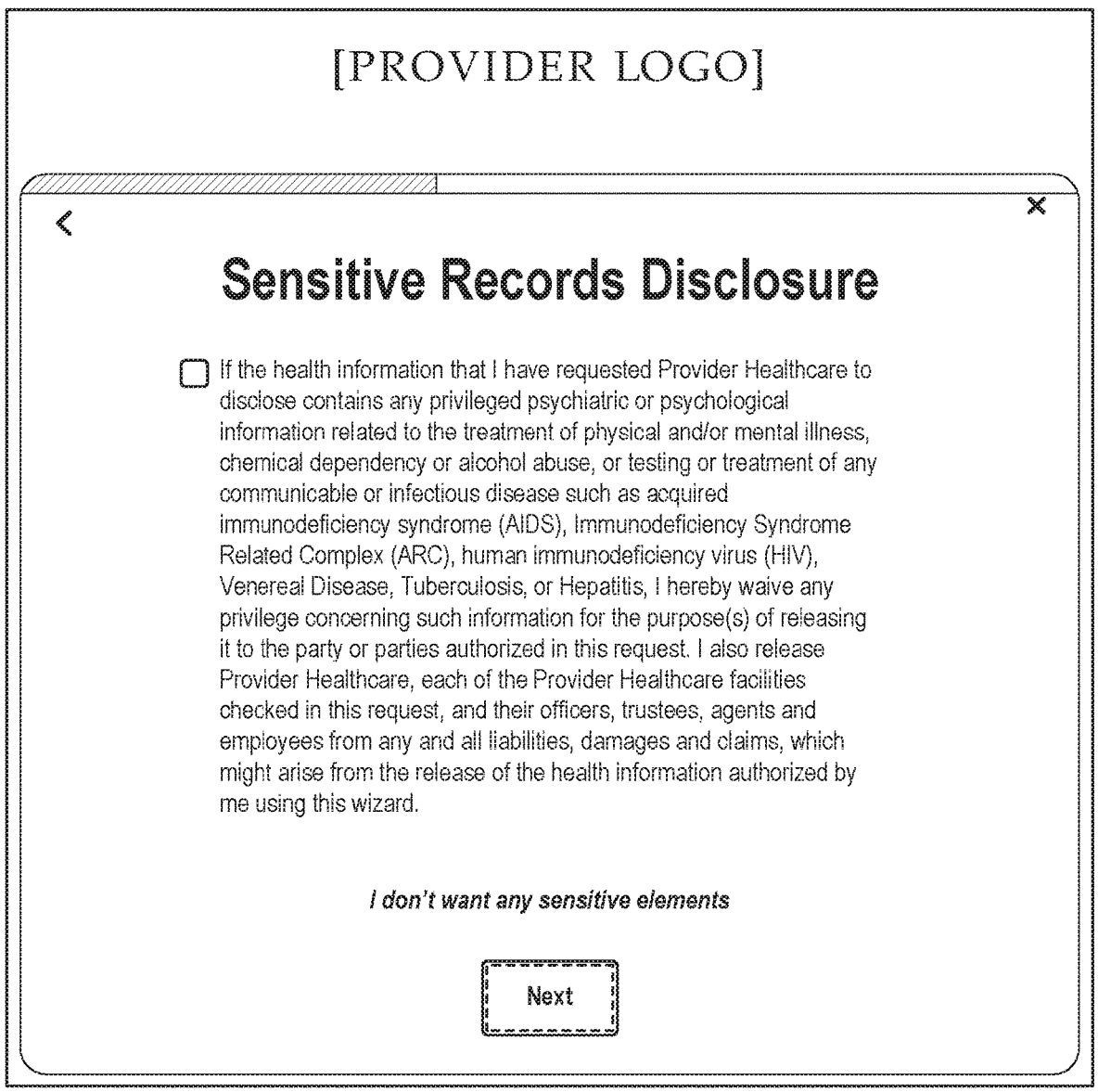
Figure 3P:
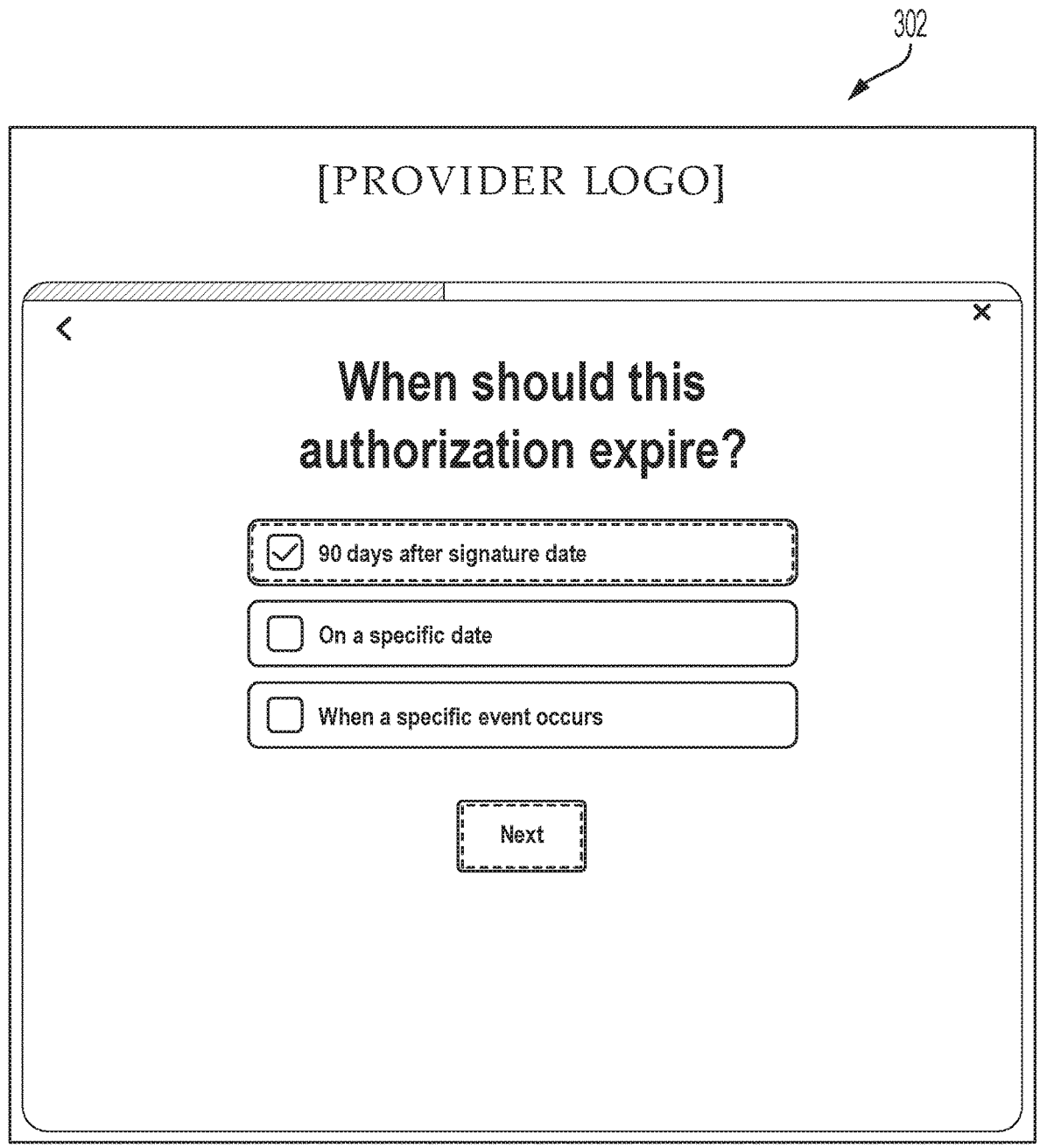
Figure 3Q:
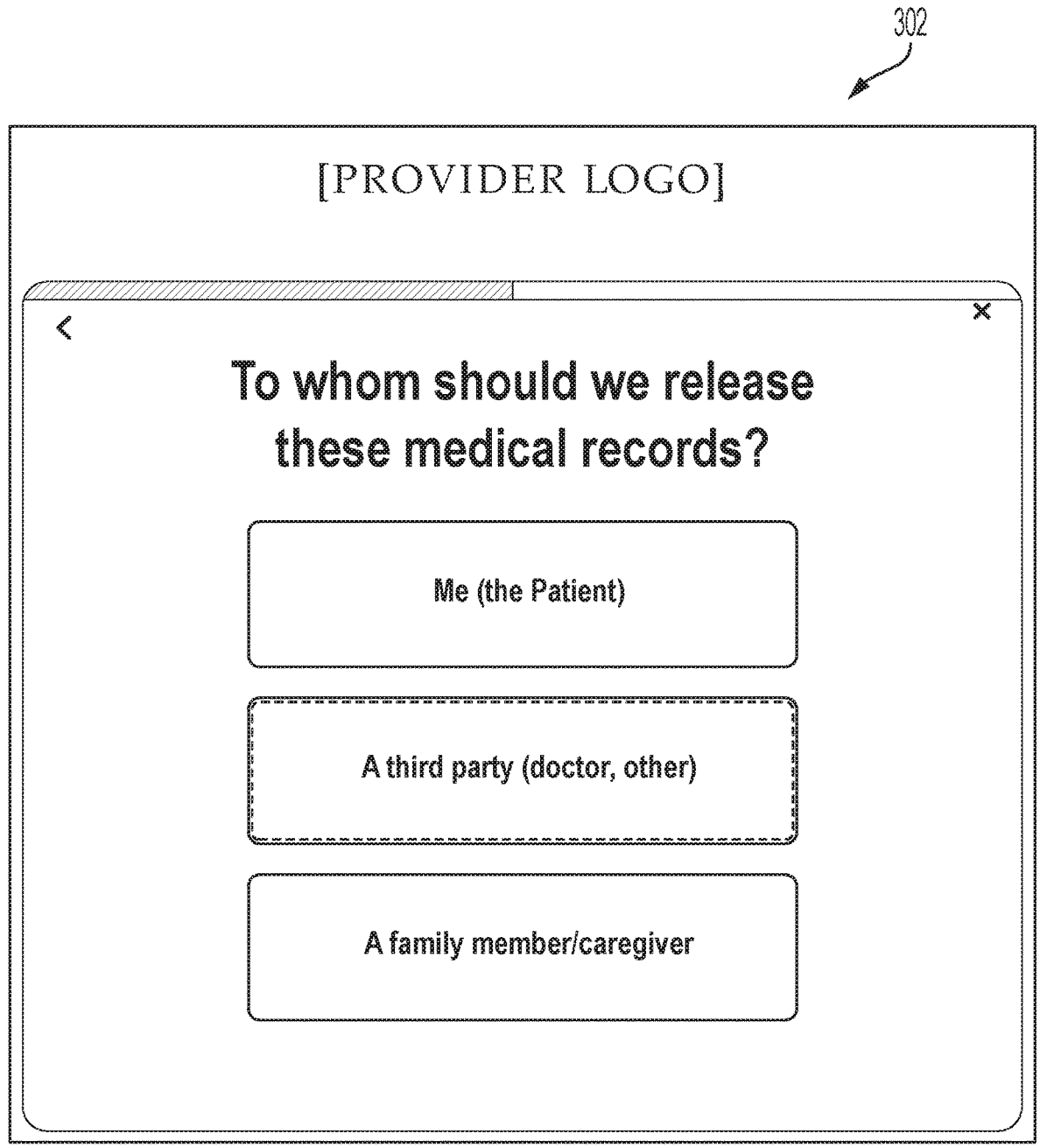
Figure 3R:
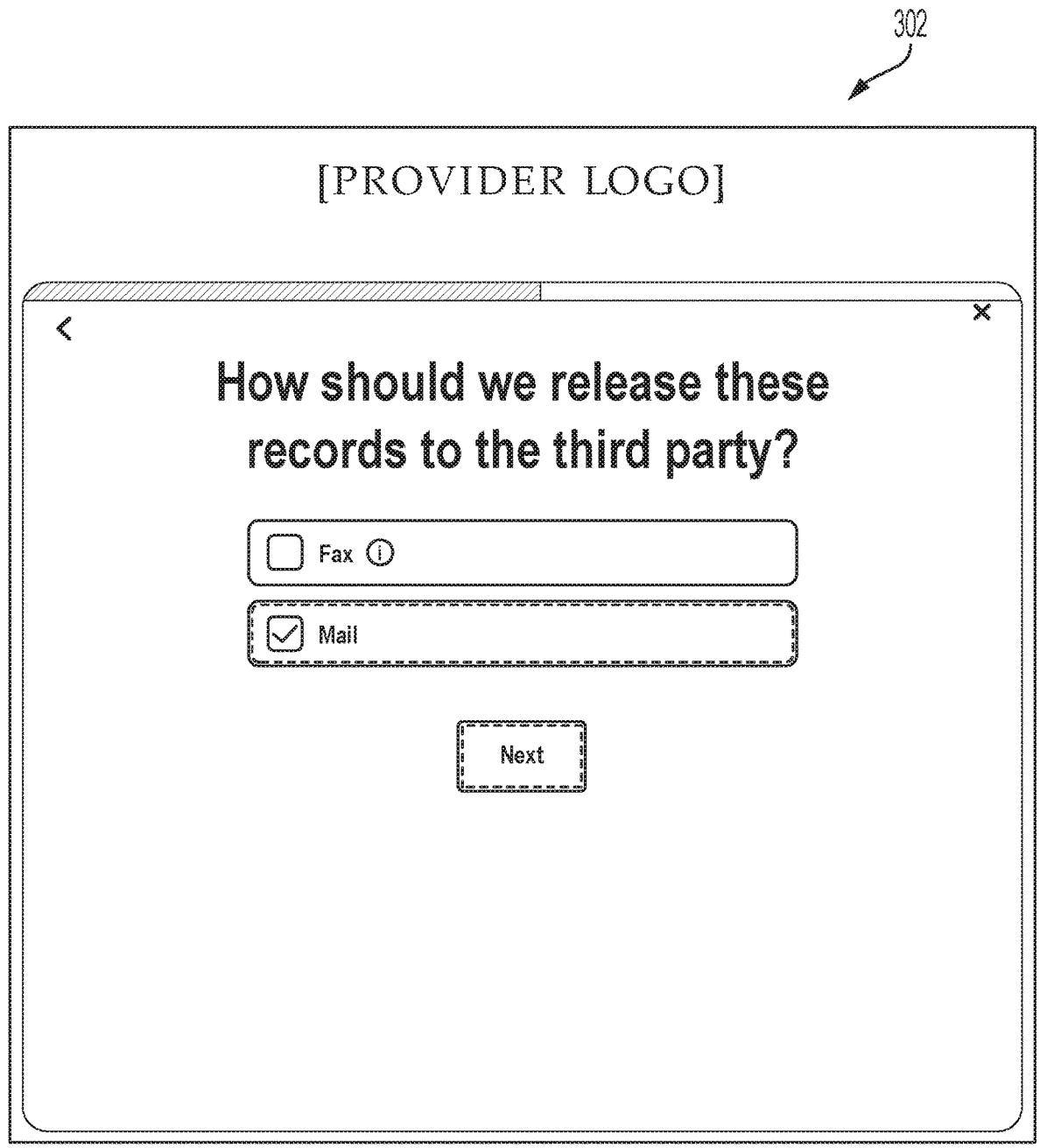
Figure 3S:
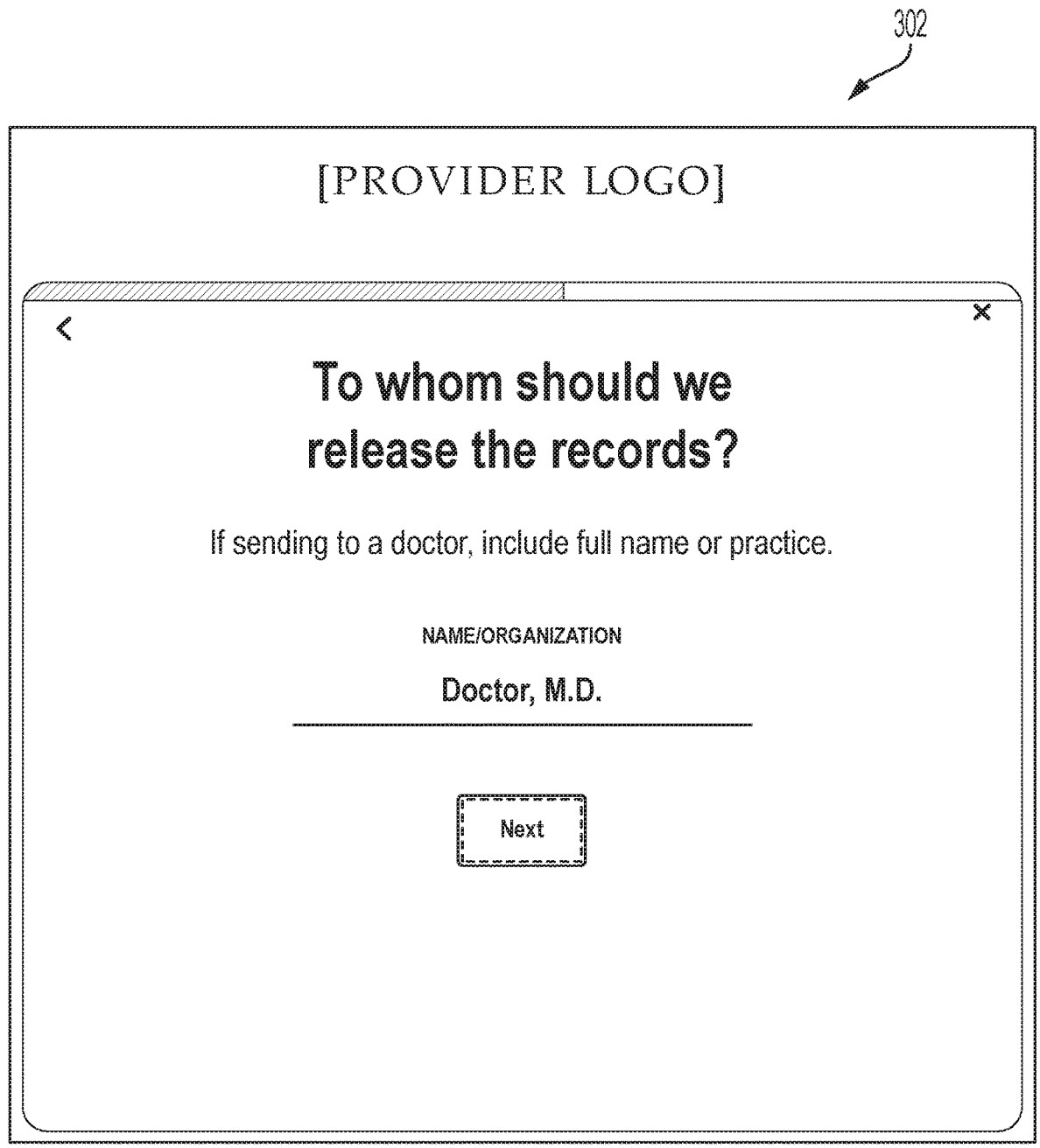
Figure 3T:
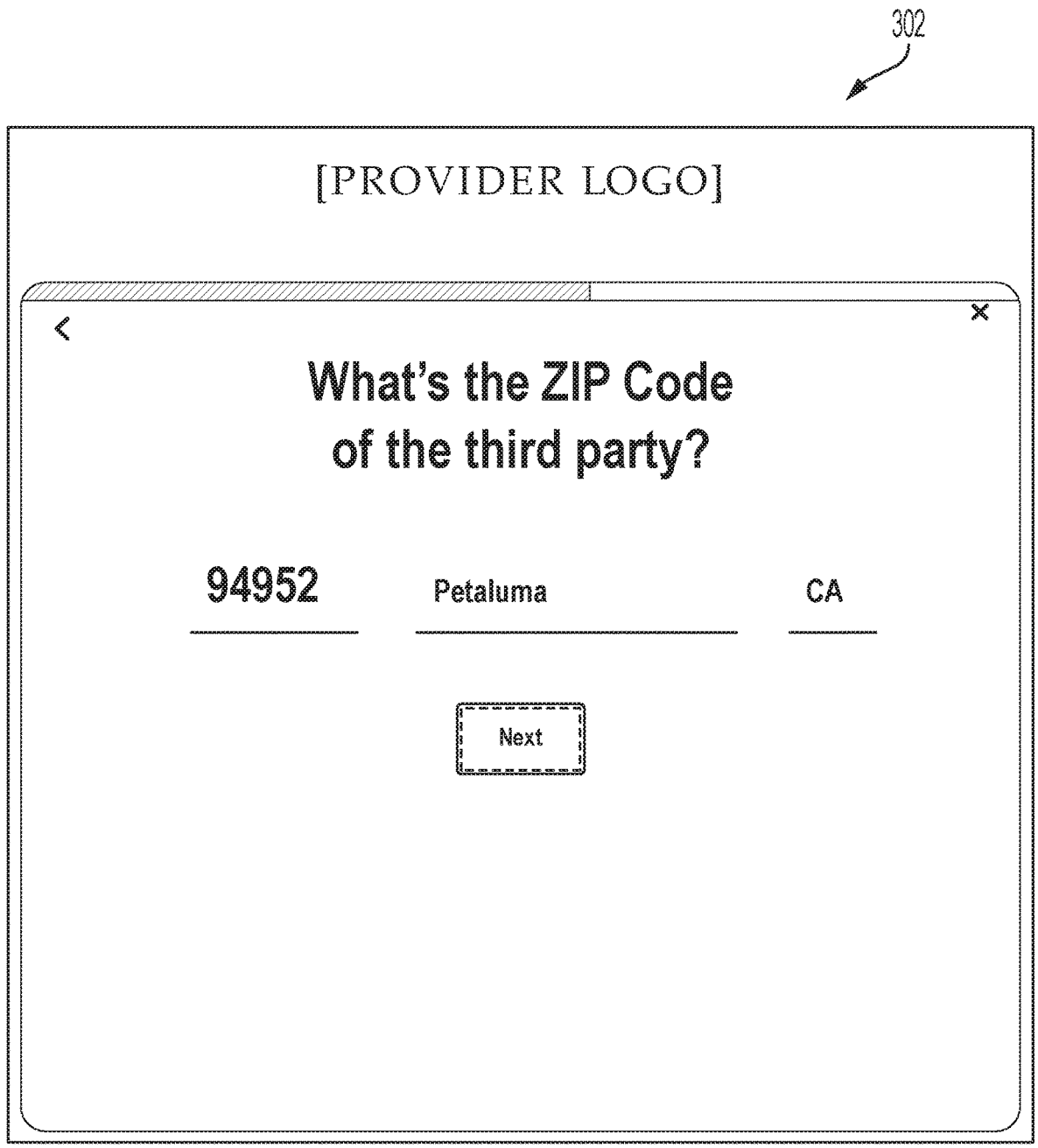
Figure 3U:
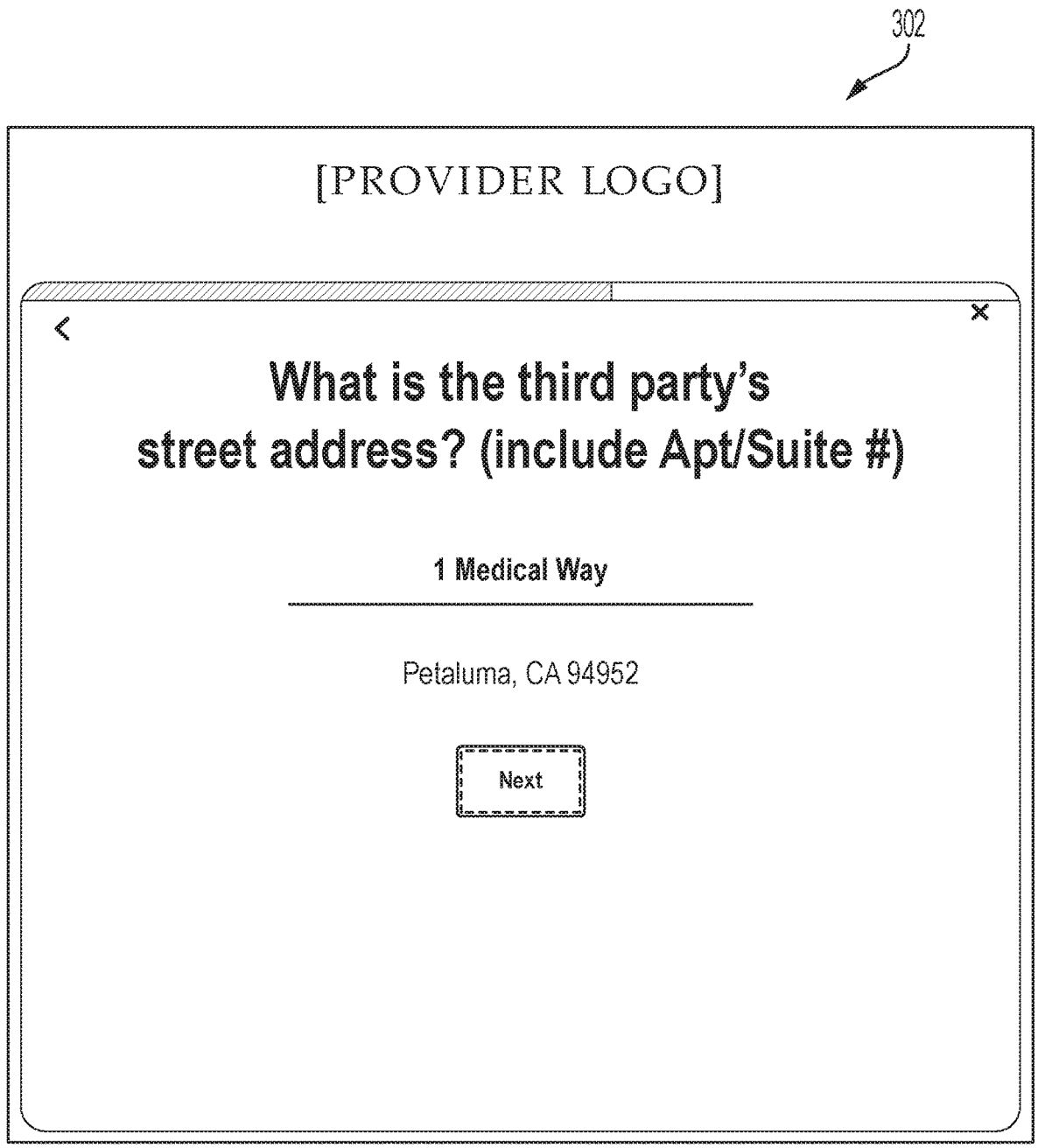
Figure 3V:
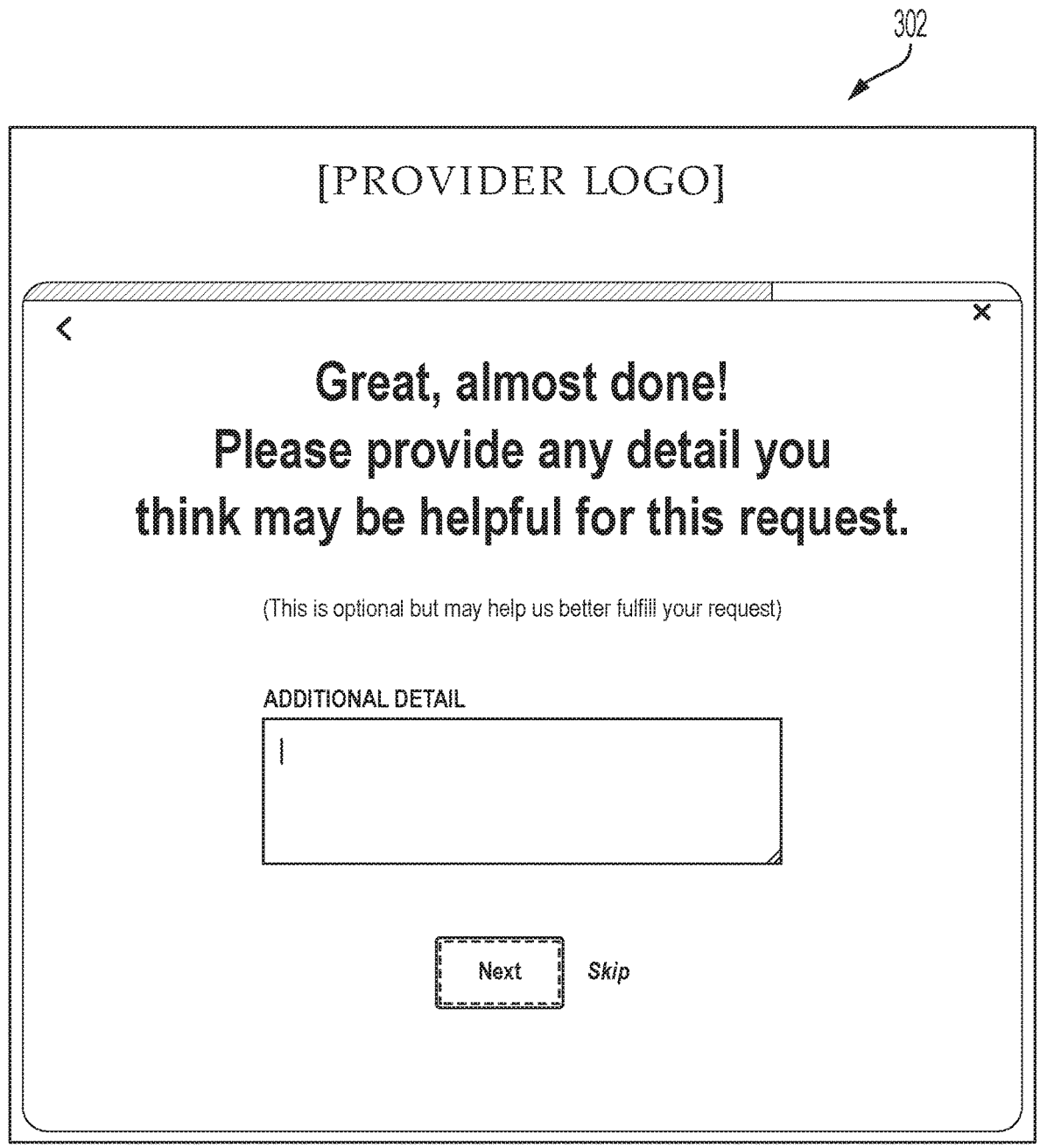
Figure 3W:
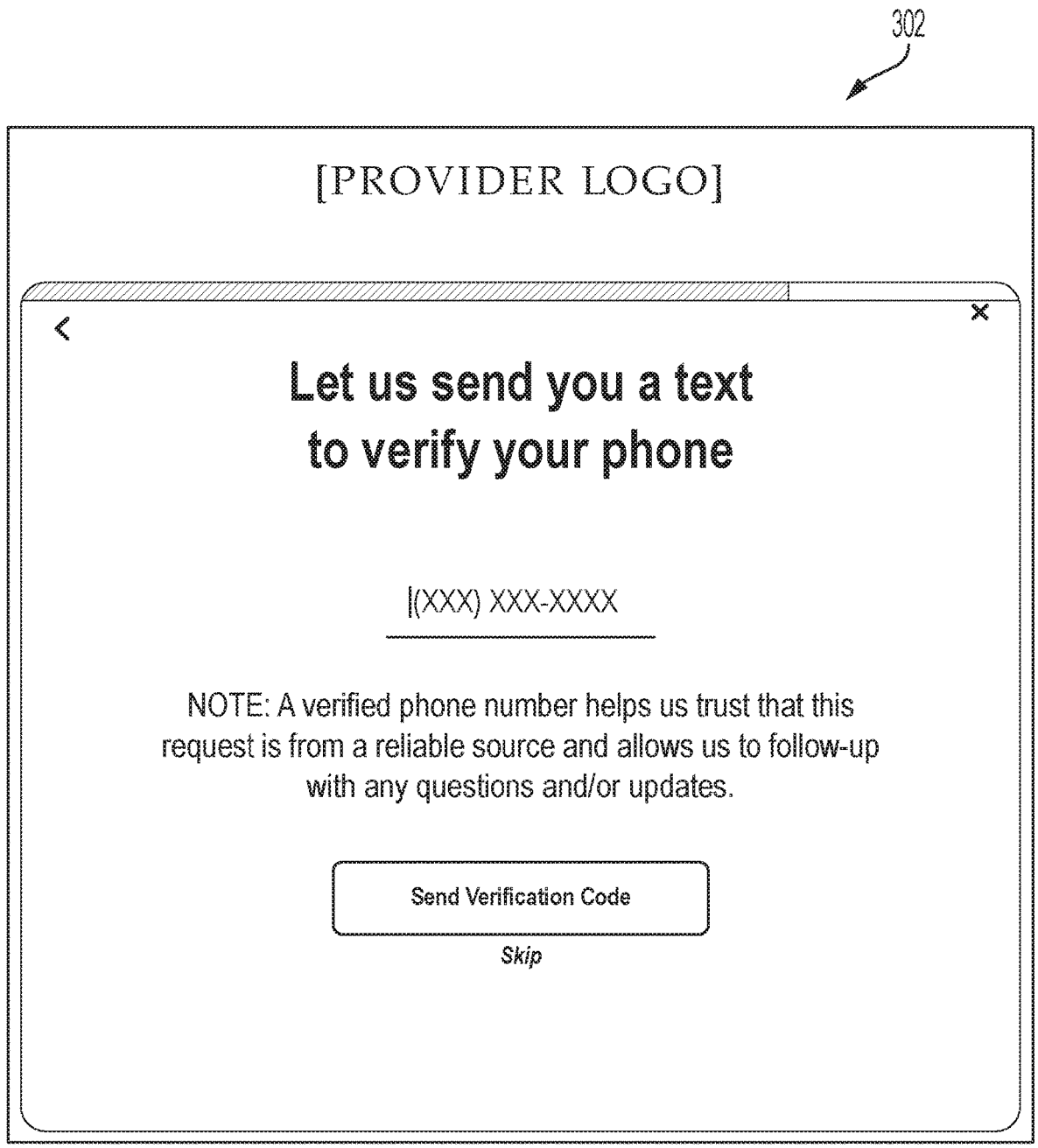
Figure 3X:
Figure 3Y:
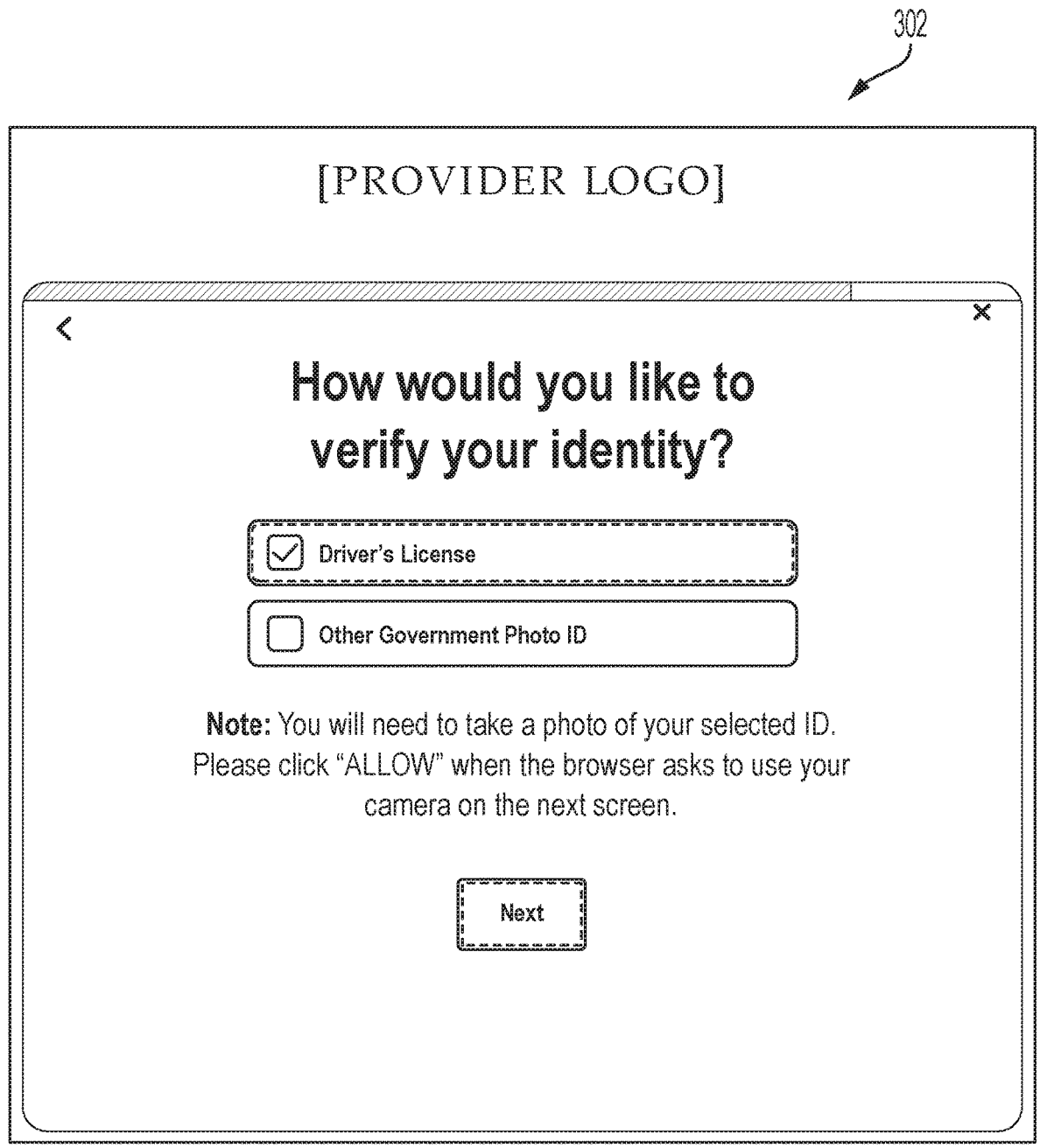
Figure 3Z:
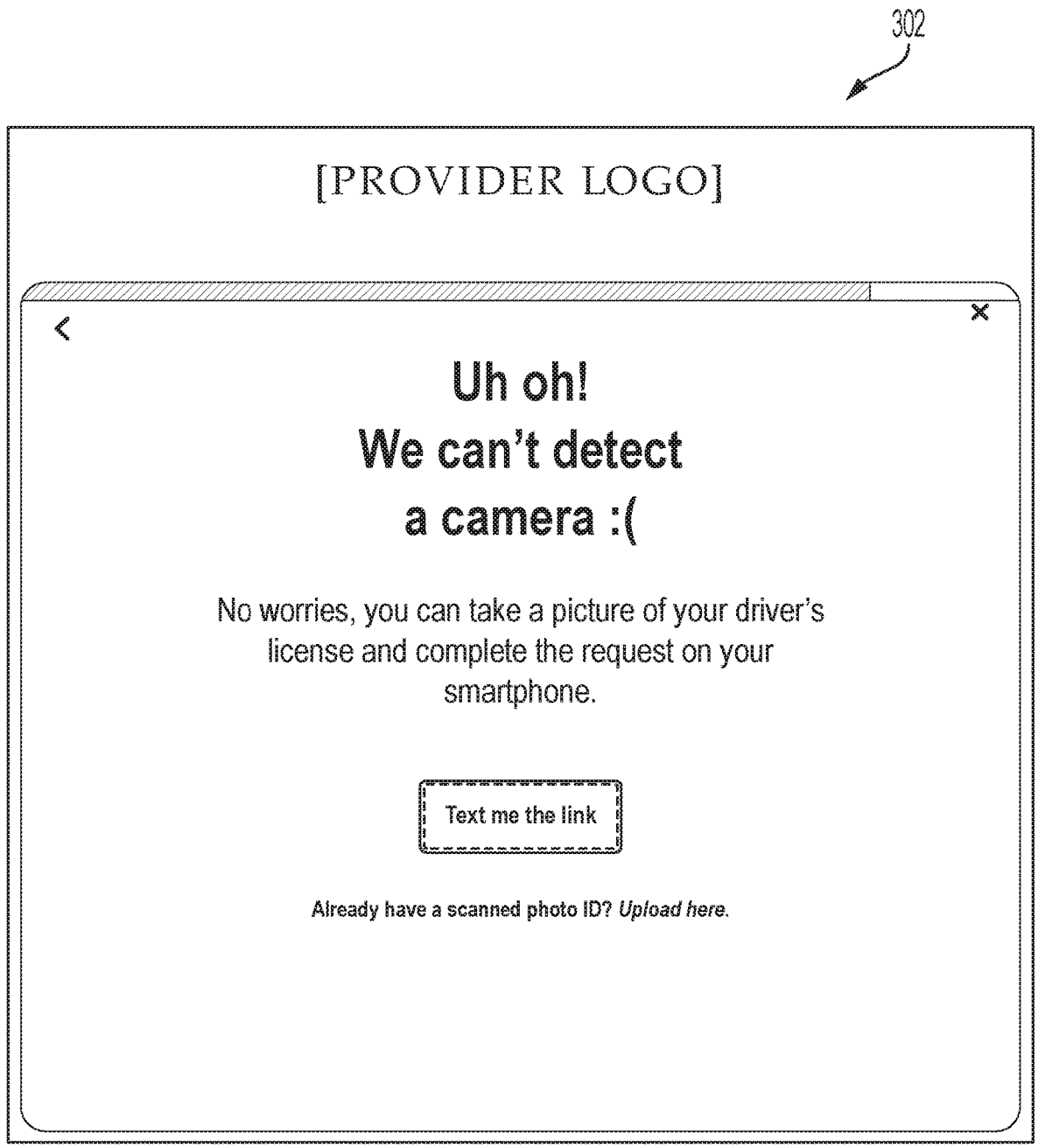
Figure 3A:
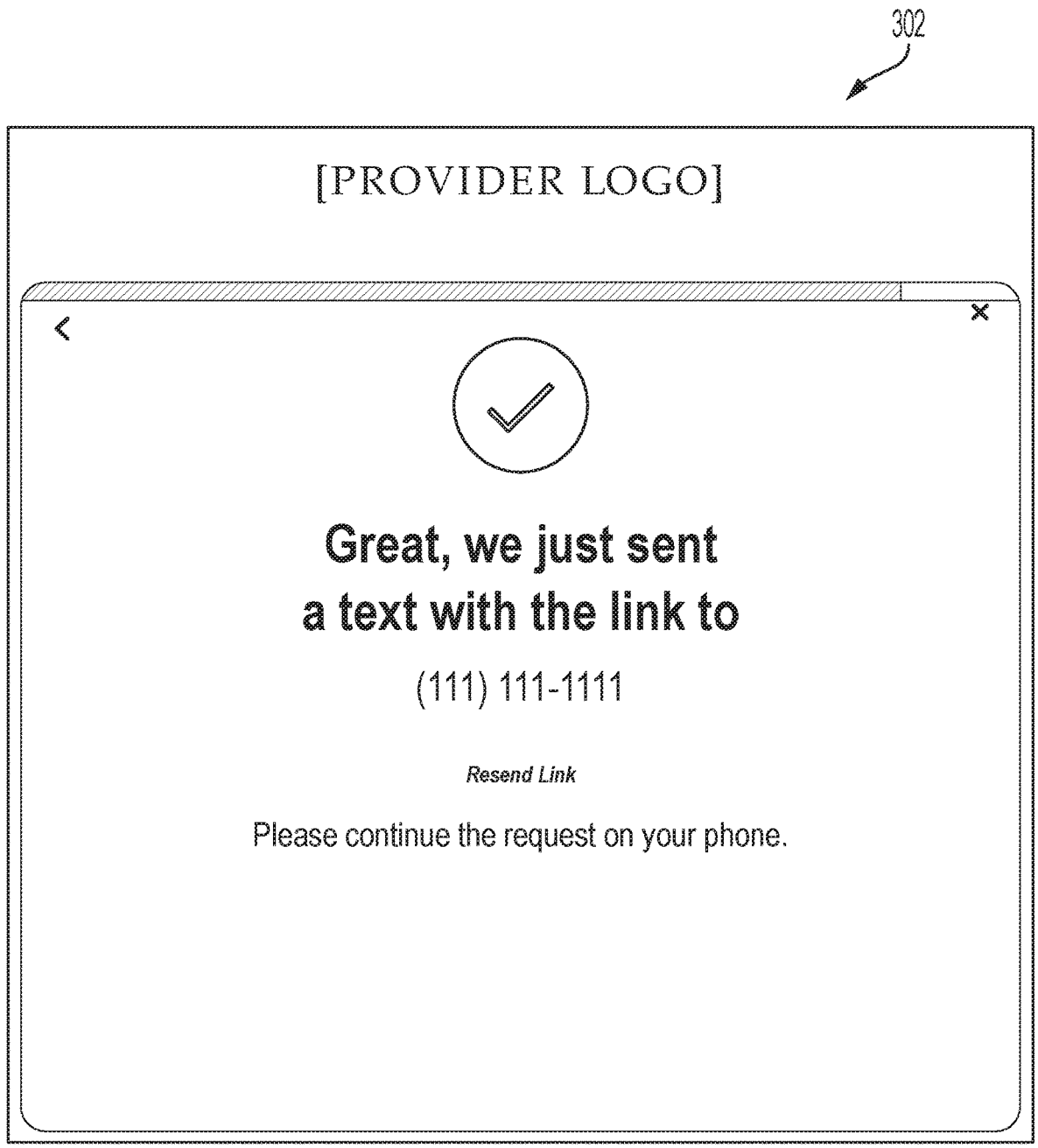
Figure 3B:
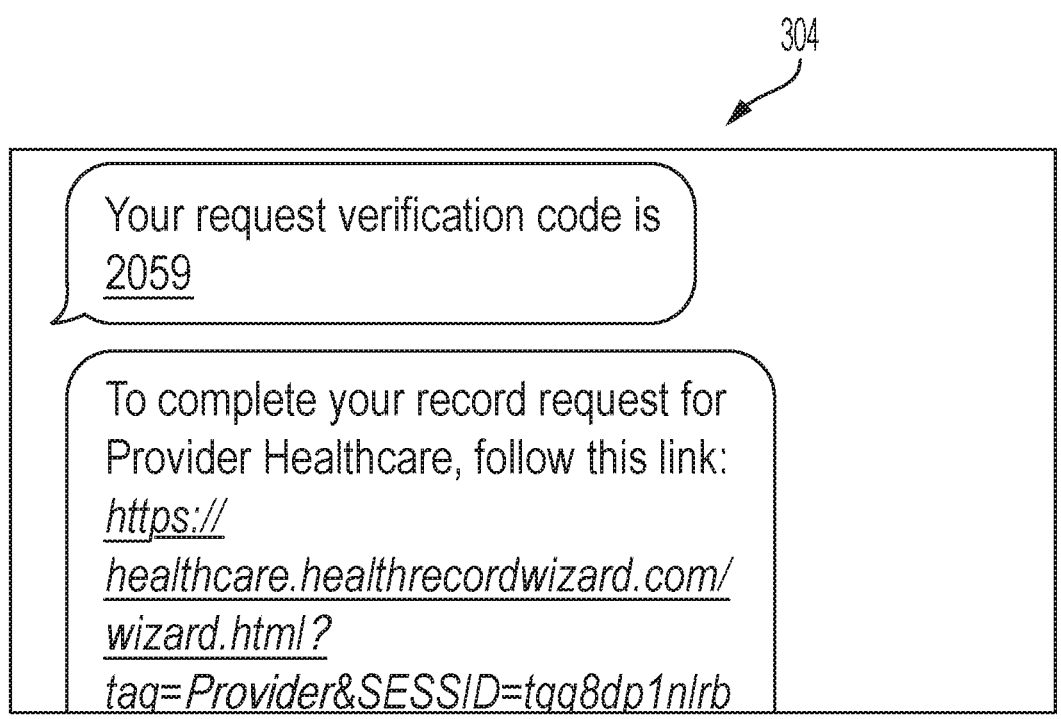
Figure 3C:
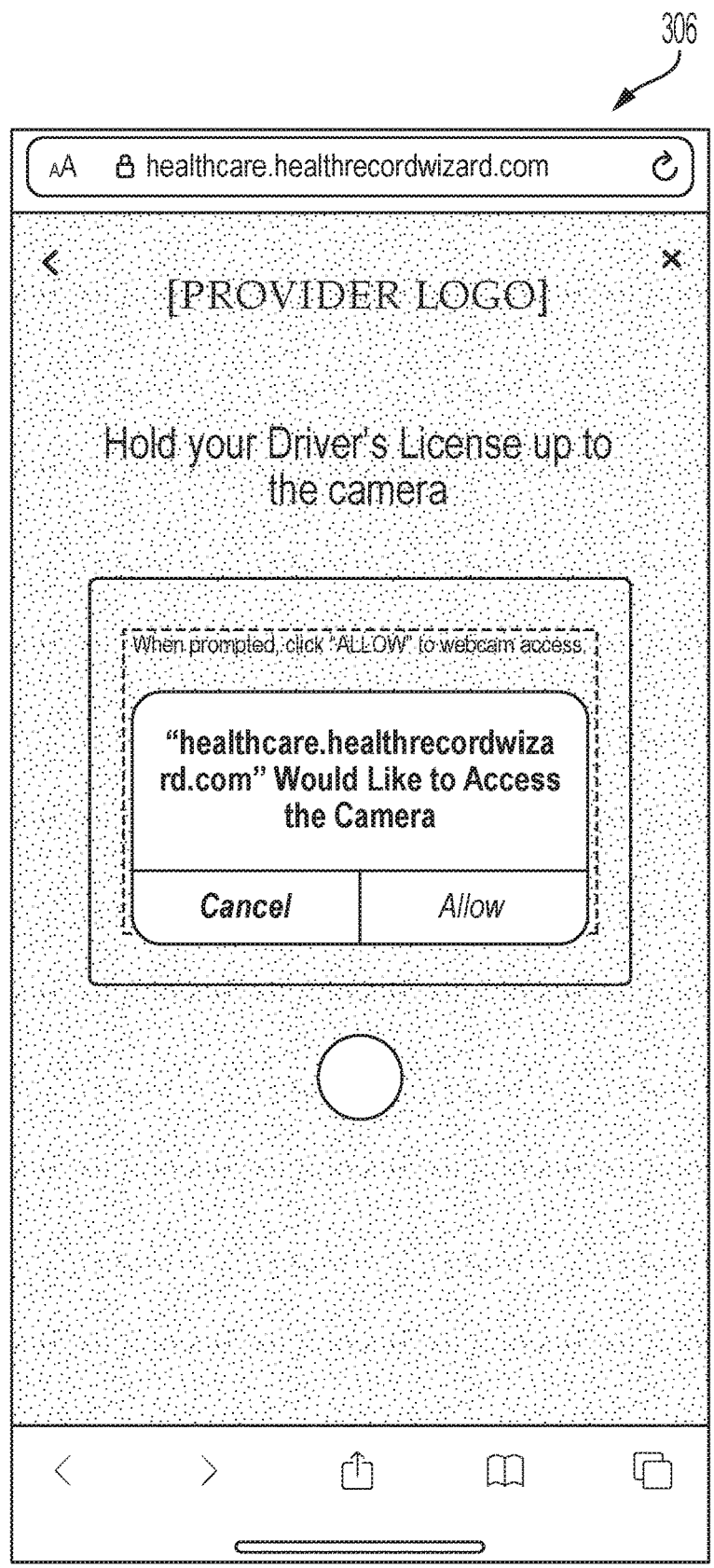
Figure 3D:
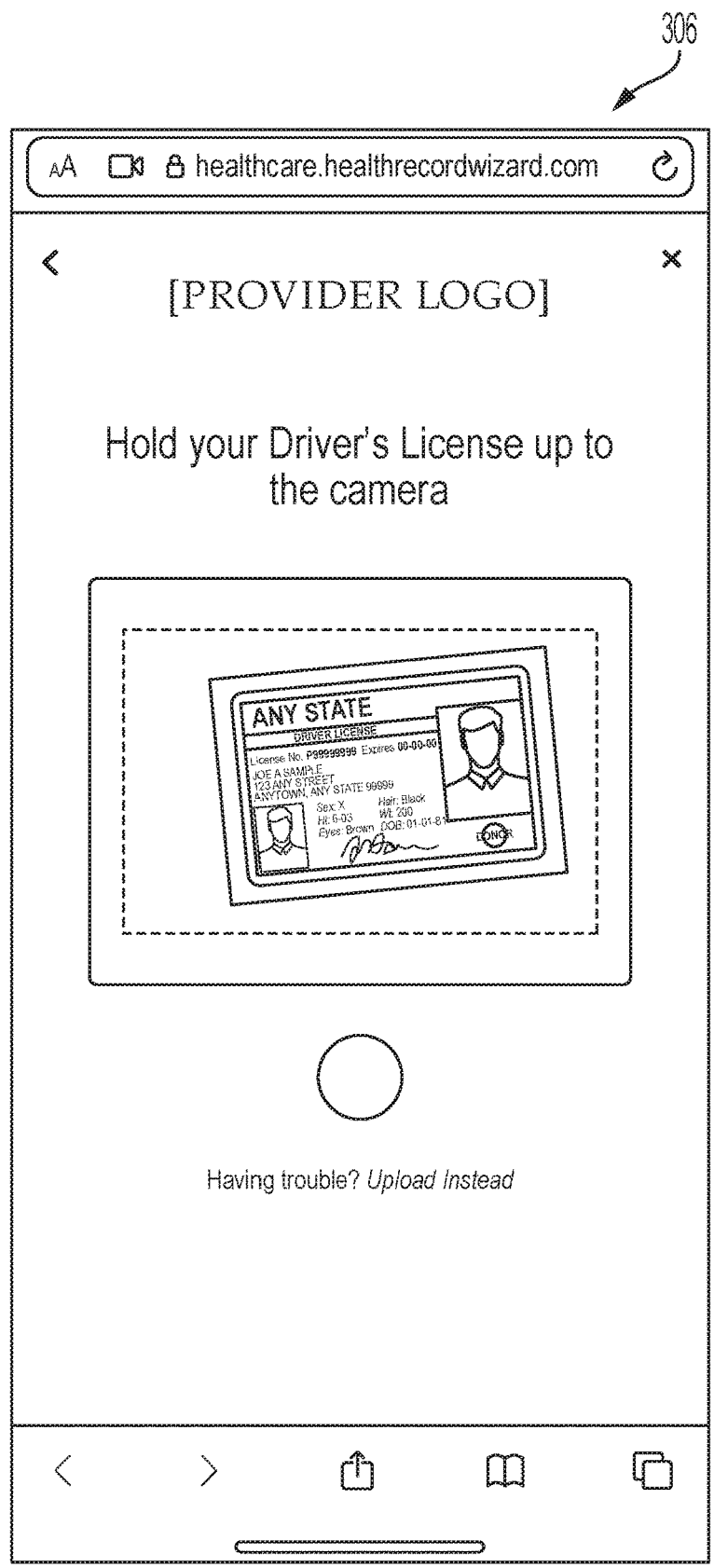
Figure 3E:
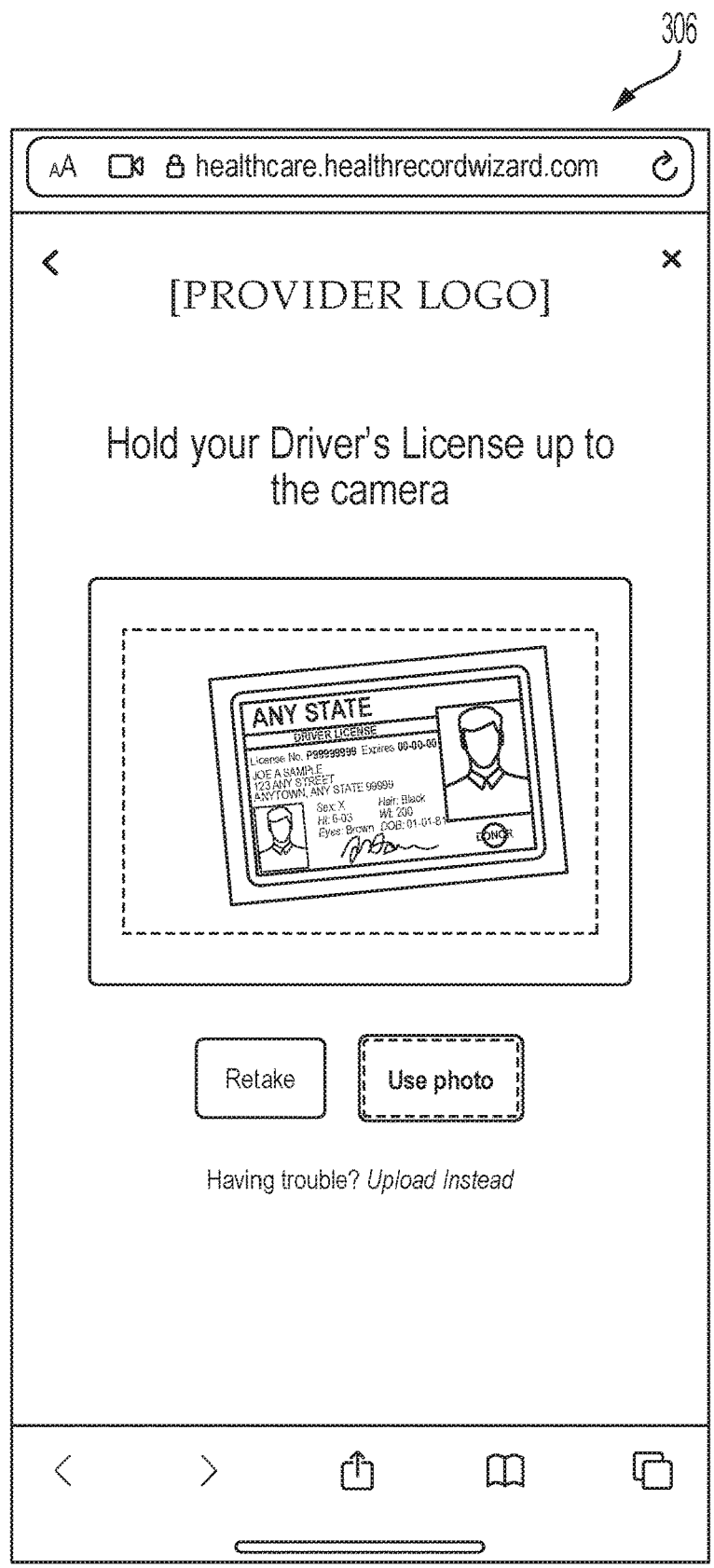

FIG. 3A illustrates an example of a structured form 300 according to an embodiment. Specifically, the structured form 300 is a medical records release authorization form (only the first page of which is illustrated here) used by the healthcare organization. Here, by way of generic example, the healthcare organization is named "Provider Healthcare." As illustrated in this example, various form fields have predetermined locations on the structured form 300, where values of those fields are expected to be provided. If the structured form 300 is a fillable PDF or other fillable document type, then those predetermined locations may be programmatically accessible via field names encoded into the document. If the structured form 300 is a flat document, then the predetermined locations may be referred to by their X, Y coordinates.

In this example, the user begins the process of requesting the medical records release using a user interface presented in a PC browser 302. A wizard (i.e., a set of code that directs a user-friendly workflow) guides the user through the process. The wizard provides initial instructions to the user (FIG. 3B), including an estimated time and requirements (photo identification and browser type) needed to complete the process. For a given healthcare organization, various locations in the user interface may include organization-specific branding. For example, in the present example, the placeholder text "[PROVIDER LOGO]" may be replaced with an organization-specific logo and/or other branding. Organization-specific branding may help provide a consistent user experience between the wizard and other interfaces associated with the healthcare organization.

In some cases, users may have the option to select which language to use when interacting with the wizard. For example, in FIG. 3B, the wizard includes a "Select Language" dropdown. Responsive to a user selecting a different language, the system may update some or all of the text displayed in the user interface with text in the selected language. To do so, the system may submit default text (e.g., prompts, instructions, button text, etc.) in a default language (e.g., English) to a translation service, receive a reply with translated text, and present the translated text in the user interface. For example, the system may submit text in the default language to an application programming interface (API) of a cloud-based translation service (e.g., the Google® Translation API and/or another cloud-based translation service). While the user interacts with the wizard in the selected language, one or more system operations may continue to use text in the default language. For example, information stored for analytics may continue to use the default language. Where users are able to provide freeform information (e.g., in a feedback text box), the system may store the information as provided; alternatively, the system may translate the information to the default language. In general, users may have the convenience of interacting with the user interface in their preferred language, while one or more parts of the system maintain the consistency of storing information in the default language.

In this example, the healthcare organization is associated with multiple facilities (e.g., hospitals, offices, affiliates, and/or another kind of facility), two or more of which may use different forms and/or requirements. In this example, multiple facilities are referred to generically as Facilities A through Q. To complete the proper form and satisfy the corresponding requirements, the wizard presents the user with a selection of facilities (FIG. 3C). The user selects the facility from which records are to be requested.

In some cases, a user may be able to request their own medical records and/or another individual's records. For example, a guardian may request records on behalf of a ward. In this example, the wizard prompts the user to indicate which type of records (i.e., their own or somebody else's) they are requesting (FIG. 3D). If the user is requesting somebody else's records, the system may request additional supplemental documentation (e.g., as described below) such as proof of guardianship or power of attorney.

In this example, the system uses email to communicate status updates to the user. In addition, the email address is a required form field. The wizard prompts the user to supply an email address (FIG. 3E). As illustrated in FIG. 3E, the wizard also prompts the user to indicate whether they wish to receive a copy of the completed request form by email. In some examples (not shown), the system may send a confirmation email to the email address provided, and the user may be required to authenticate their email address by following a link provided in the email.

Figure 3F:
Figure 3G:
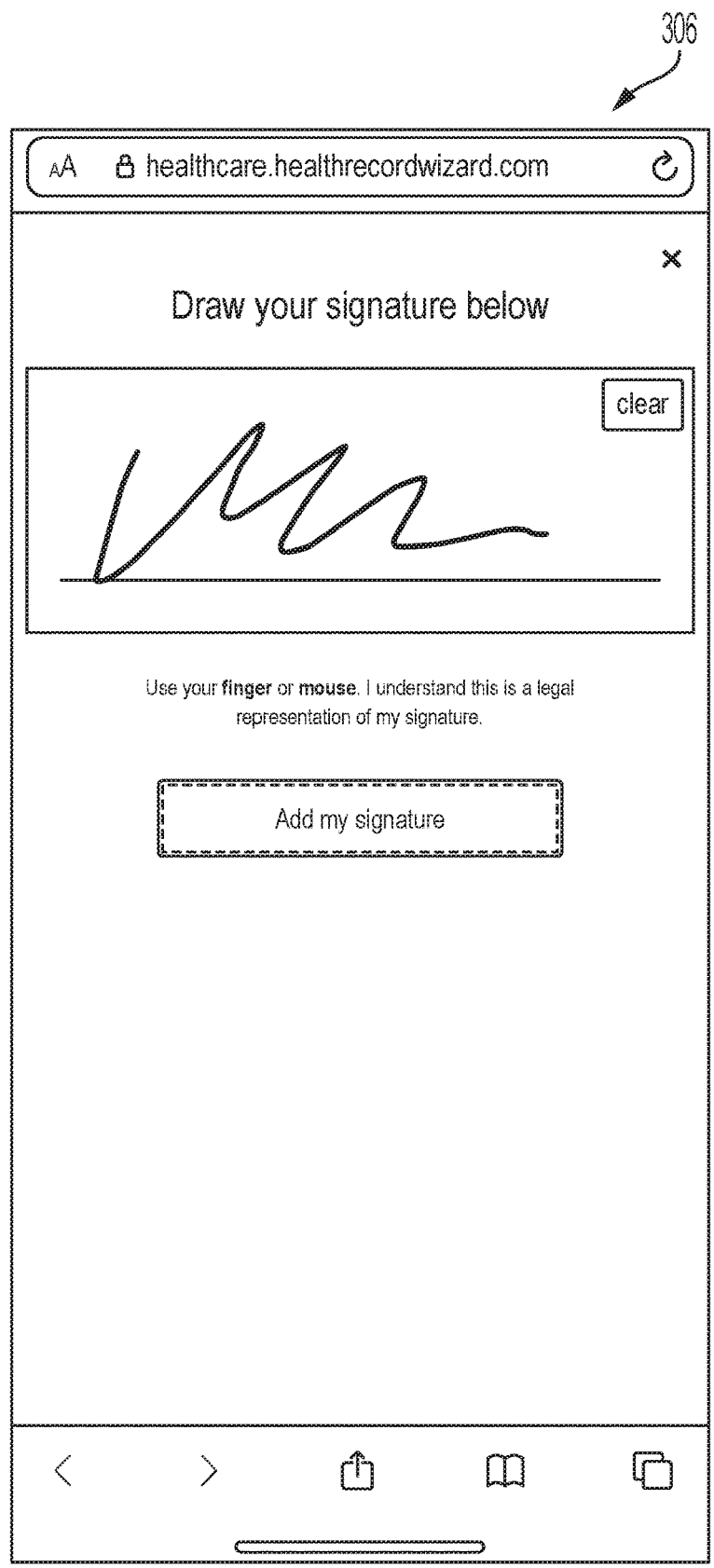
Figure 3H:
Figure 3I:
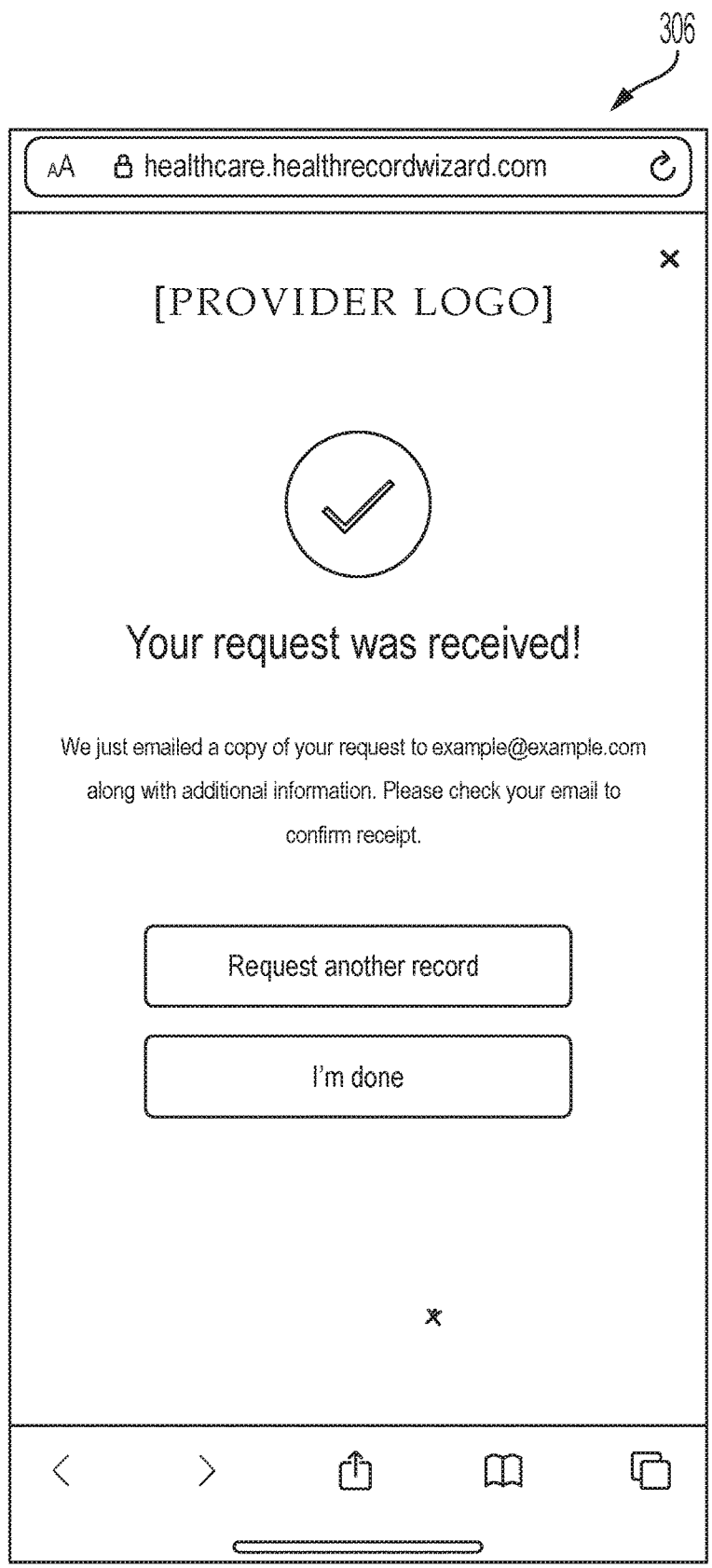
Figure 3J:
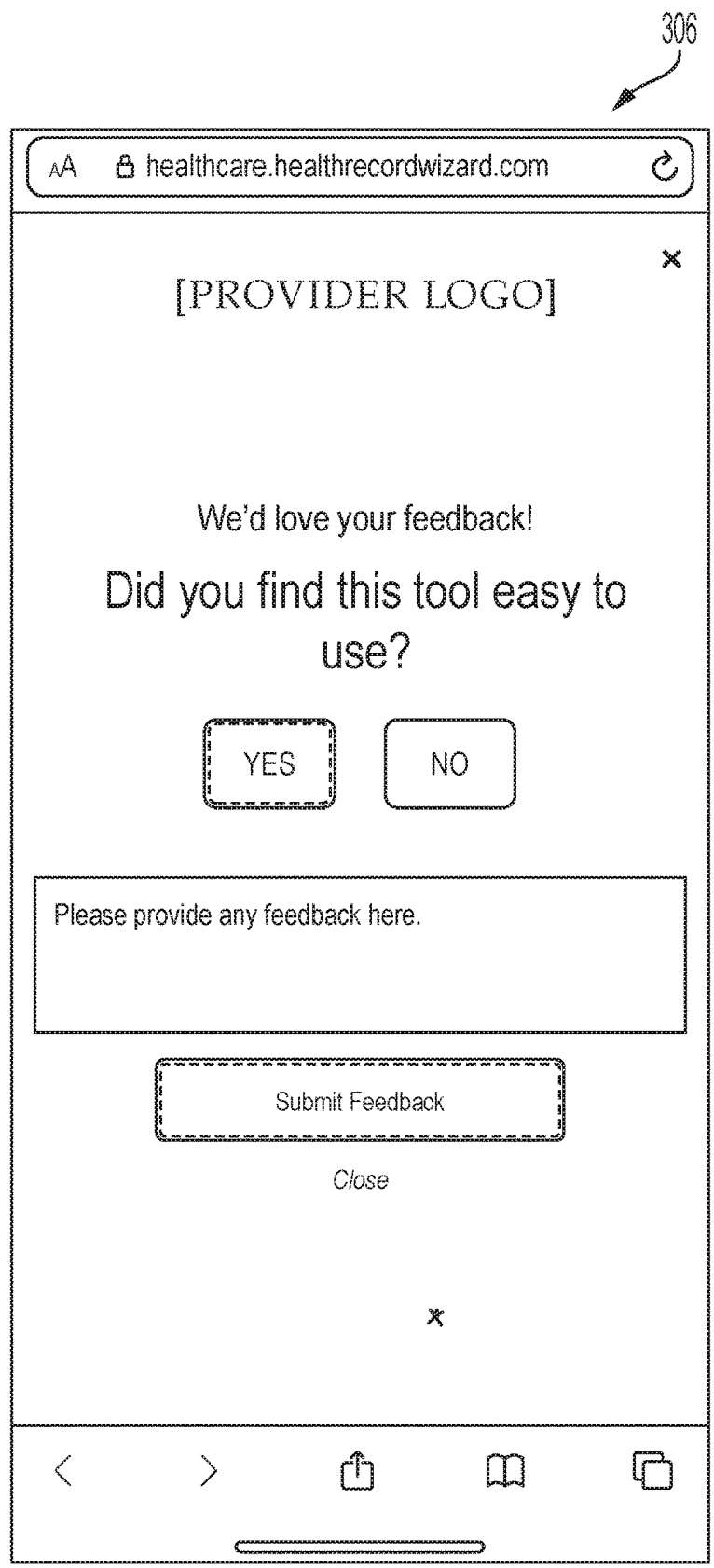
Figure 3K:
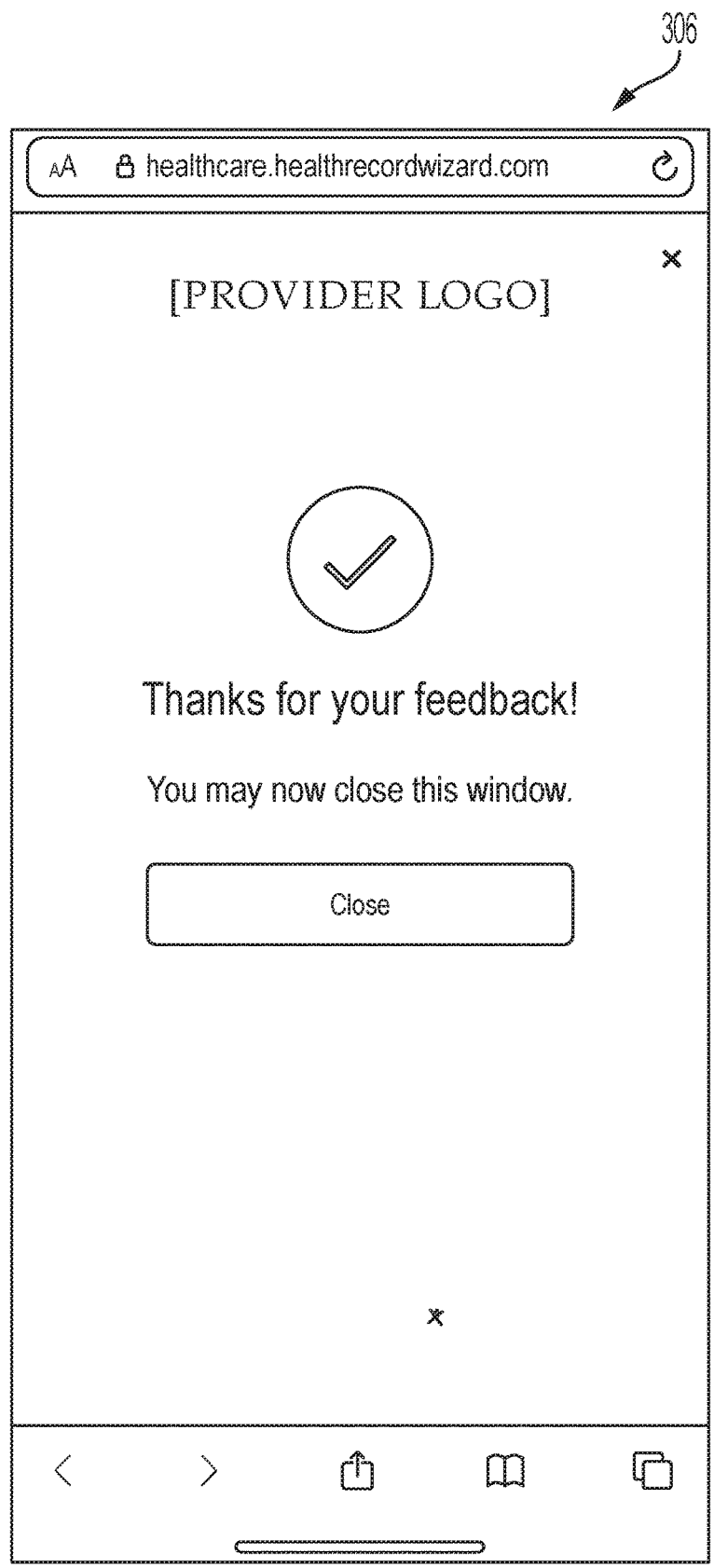
Figure 3M:
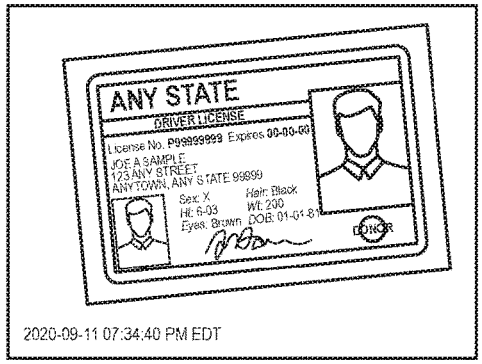

In this example, the wizard presents a series of screens to the user, via the PC browser 302, to obtain information required for the form. Specifically, the wizard obtains the user's full legal name (FIG. 3F), zip code (FIG. 3G), street address (FIG. 3H), and date of birth (FIG. 3I). As illustrated in FIG. 3F, the wizard gives the user the option to indicate that their name has changed, in which case they may be asked to also provide their prior legal name. Obtaining information about a name change may help the healthcare provider locate records where the name at time of service does not match the patient's current legal name.

In this example, the wizard asks the user to indicate the reason for requesting records (FIG. 3J). As discussed above, the reason may help the system determine a recommended and/or default set of records to designate in the request. The wizard also asks the user to indicate a timeframe for the records (FIG. 3K). After selecting a general timeframe, the wizard gives the user the option to further narrow the timeframe of the request to one or more specific dates (FIG. 3L). For example, if a user is requesting records associated with a workplace injury that occurred in the last six months, then it is not necessary to request records for an entire year. Limiting the timeframe of the records requested may reduce costs and/or help expedite processing. Once the reason(s) and timeframe for the request have been determined, the wizard alerts the user (FIG. 3M) that a recommended set of records has been selected. The wizard then gives the user the option to make changes to the recommended set of records (FIG. 3N), indicate whether to request the release of sensitive records (FIG. 3O), and indicate when the release authorization should expire (FIG. 3P).

In this example, the system allows the user to request the release of records to themselves, a third party, or a family member/caregiver (FIG. 3Q). Depending on who is to receive the records, the wizard will request corresponding contact information. In this example, the user requests that the records be released to a third party. The wizard then requests how the third party should receive the records (i.e., by fax or mail) (FIG. 3R). In this example, email is not available as an option to release records to a third party. Email may be available as a delivery option in other examples and/or for different types of recipients.

In this example, the wizard proceeds to request contact information for the records recipient. Specifically, the wizard obtains the recipient's name/organization (FIG. 3S), zip code (FIG. 3T), and street address (FIG. 3U). The wizard also gives the user the option to provide a note with additional information about the request (FIG. 3V). For example, the user may clarify the reason for the request, which may help the healthcare provider locate and release the corresponding record(s).

In this example, the system offers mobile phone number authentication whether or not the user intends to use a mobile device to capture an image of supplemental documentation. Specifically, the wizard prompts the user to supply a mobile phone number to be verified (FIG. 3W). A verified mobile phone number may allow the system to send text messages with information about the request such as confirmations, status updates, etc. As illustrated in FIG. 3W, the user may alternatively choose to skip the verification process. When the user enters a mobile phone number, the system sends a text message to the user (seen in FIG. 3BB, discussed in further detail below) with a confirmation code. The system prompts the user (FIG. 3X) to enter the confirmation code to verify the phone number.

In this example, the records request requires proof of identity in the form of a driver's license or other government-provided photo identification. The wizard prompts the user (FIG. 3Y) to indicate what kind of proof they would like to provide. The wizard also informs the user that they will need to take a photo of the selected form of identification. In this example, the system first attempts to access a camera on the current device (e.g., a webcam that is accessible to the PC browser 302). However, no such device is detected. Accordingly, the wizard informs the user (FIG. 3Z) that they have the option of taking a picture using their mobile device instead. The user can request that the system text a link to the verified mobile phone number. Alternatively, the user can choose to upload an existing image of photo identification. For example, the user may have a scanned copy of their driver's license stored in a folder on their PC. In this example, the user chooses to complete the process on the verified mobile device, and the wizard provides instruction for continuing the process on the mobile device (FIG. AA).

FIG. 3BB illustrates an example of a messaging interface 304 on the user's mobile device. The user has received two text messages from the system: the confirmation code to verify the mobile phone number, as discussed above; and a subsequent link to an image capture interface. Specifically, when the user selects the link in the messaging interface 304, the image capture interface loads in a mobile browser 306 (FIG. 3CC). If necessary, the mobile browser 306 prompts the user to authorize access to the mobile device's camera. The user then orients the mobile device to capture a live (i.e., currently captured, not prerecorded) image of the photo identification, in this example a driver's license (FIG. 3DD). When the user selects/taps the control to capture the image, the wizard (now operating on the user's mobile device) prompts the user to indicate whether they want to use that image or capture a new image (FIG. 3EE).

Once the user captures and confirms an image, in this example, the system has all the information it needs to present a preview of the form and supplemental documentation (FIG. 3FF). The user may have the option to revise information that was already provided, including information that was provided via the PC browser 302. The user may be able to scroll down to view all pages of the populated form, as well as the supplemental documentation image (not shown in FIG. 3FF). If the user approves the form and supplemental documentation, then the user proceeds to provide an electronic signature (FIG. 3GG). The system adds the electronic signature to the preview and gives the user another chance to review/edit (FIG. 3HH) before submitting the records release request.

After the user submits the request, the system generates and transmits a form bundle as described above, including emailing a copy of the request to the user. In addition, the wizard provides the user the option to prepare another request or indicate that they are done (FIG. II). If the user chooses to prepare another request, the new request may be prepopulated with information (e.g., the user's name and contact information) that was already provided for the just-completed request. The user may not be required to reverify their mobile phone number. If the user indicates that they are done, then the wizard proceeds to prompt them for feedback (FIG. 3JJ). After the user provides feedback (or declines to provide feedback), the wizard indicates that the process is complete (FIG. 3KK).

FIG. 3LL illustrates an example of a populated form 308, as received in a PDF at the user's email after completing the example process described above. Specifically, the populated form 308 is an electronically populated version of the structured form 300 illustrated in FIG. A. The PDF also includes unstructured data, i.e., supplemental documentation 310 as illustrated in FIG. 3MM. In this example, the supplemental documentation 310 includes the captured live image of the user's driver's license and unstructured (i.e., outside the structured format of the form) copies of information included in the form: contact information; signature; and reason for the request. Thus, in this example, the system quickly prepared a form bundle that included the structured and unstructured information needed to complete a medical records release request.

5. Miscellaneous

In an embodiment, a system includes one or more devices, including one or more hardware processors, that are configured to perform any of the operations described herein and/or recited in any of the claims.

In an embodiment, one or more non-transitory computer-readable storage media store instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

6. Computing Devices

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 4:
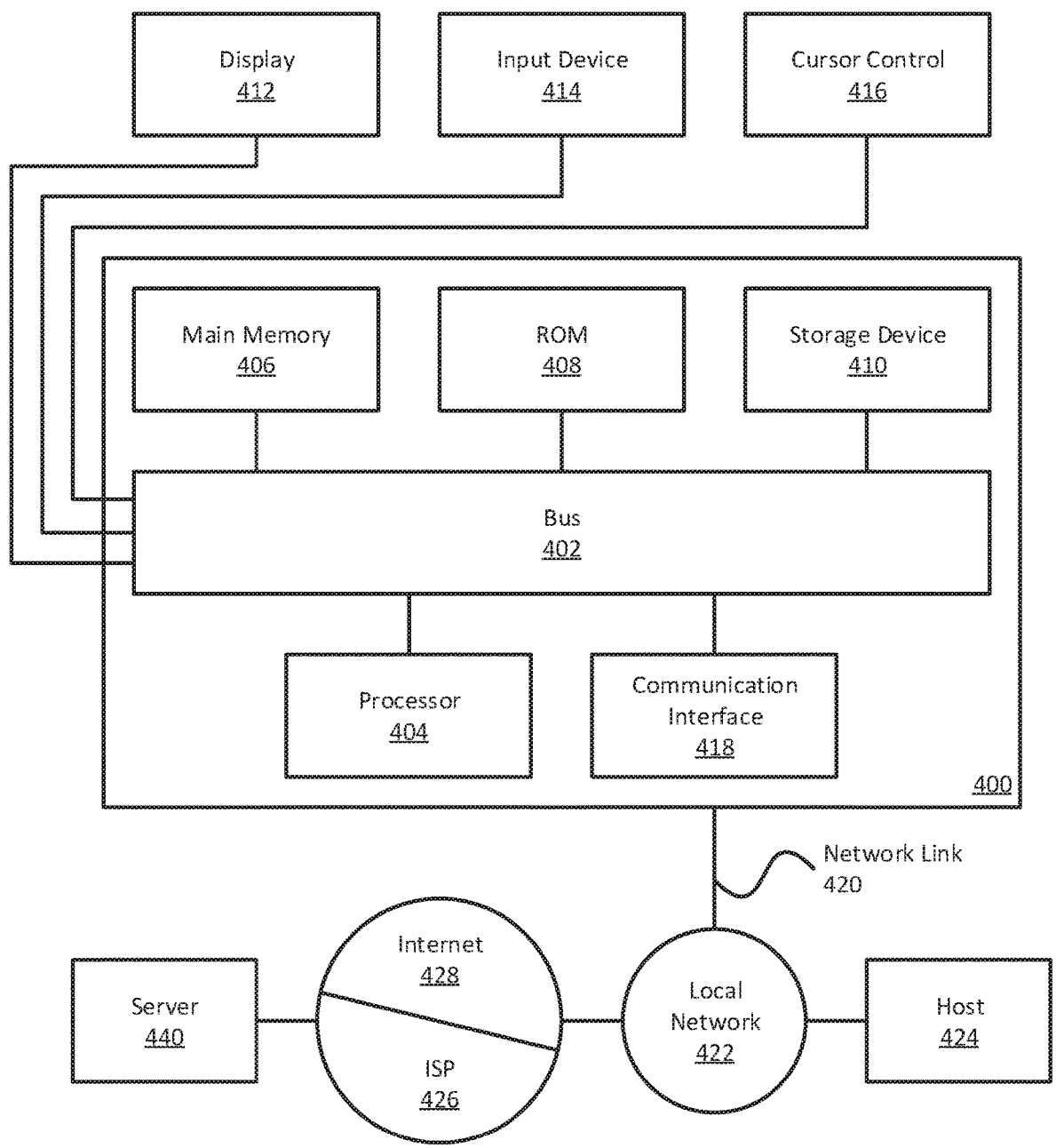
FIG. 4 is a block diagram of an example of a computer system according to an embodiment.

For example, FIG. 4 is a block diagram of an example of a computer system 400 according to an embodiment. Computer system 400 includes a bus 402 or other communication mechanism for communicating information, and a hardware processor 404 coupled with the bus 402 for processing information. Hardware processor 404 may be a general-purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in one or more non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk or optical disk, is provided and coupled to bus 402 for storing information and instructions.

Computer system 400 may be coupled via bus 402 to a display 412, such as a liquid crystal display (LCD), plasma display, electronic ink display, cathode ray tube (CRT) monitor, or any other kind of device for displaying information to a computer user. An input device 414, including alphanumeric and other keys, may be coupled to bus 402 for communicating information and command selections to processor 404. Alternatively or additionally, computer system 400 may receive user input via a cursor control 416, such as a mouse, a trackball, a trackpad, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. Alternatively or additionally, computer system 3 may include a touchscreen. Display 412 may be configured to receive user input via one or more pressure-sensitive sensors, multi-touch sensors, and/or gesture sensors. Alternatively or additionally, computer system 400 may receive user input via a microphone, video camera, and/or some other kind of user input device (not shown).

Computer system 400 may implement the techniques described herein using customized hard-wired logic, one or more ASICs or FPGAs, firmware, and/or program logic which in combination with other components of computer system 400 causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 410. Volatile media includes dynamic memory, such as main memory 406. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 402. Transmission media may also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 400 may receive the data from the network and place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422, and communication interface 418.

The received code may be executed by processor 404 as it is received, and/or stored in storage device 410, or other non-volatile storage for later execution.

7. Computer Networks

In an embodiment, a computer network provides connectivity among a set of nodes running software that utilizes techniques as described herein. The nodes may be local to and/or remote from each other. The nodes are connected by a set of links. Examples of links include a coaxial cable, an unshielded twisted cable, a copper cable, an optical fiber, and a virtual link.

A subset of nodes implements the computer network. Examples of such nodes include a switch, a router, a firewall, and a network address translator (NAT). Another subset of nodes uses the computer network. Such nodes (also referred to as "hosts") may execute a client process and/or a server process. A client process makes a request for a computing service (for example, a request to execute a particular application and/or retrieve a particular set of data). A server process responds by executing the requested service and/or returning corresponding data.

A computer network may be a physical network, including physical nodes connected by physical links. A physical node is any digital device. A physical node may be a function-specific hardware device. Examples of function-specific hardware devices include a hardware switch, a hardware router, a hardware firewall, and a hardware NAT. Alternatively or additionally, a physical node may be any physical resource that provides compute power to perform a task, such as one that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (for example, a physical network). Each node in an overlay network corresponds to a respective node in the underlying network. Accordingly, each node in an overlay network is associated with both an overlay address (to address the overlay node) and an underlay address (to address the underlay node that implements the overlay node). An overlay node may be a digital device and/or a software process (for example, a virtual machine, an application instance, or a thread) A link that connects overlay nodes may be implemented as a tunnel through the underlying network. The overlay nodes at either end of the tunnel may treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware and/or software configured to execute server processes. Examples of network resources include a processor, a data storage, a virtual machine, a container, and/or a software application. Network resources may be shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). In a hybrid cloud, a computer network includes a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, a system supports multiple tenants. A tenant is a corporation, organization, enterprise, business unit, employee, or other entity that accesses a shared computing resource (for example, a computing resource shared in a public cloud). One tenant (through operation, tenant-specific practices, employees, and/or identification to the external world) may be separate from another tenant. The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In an embodiment, in a multi-tenant computer network, tenant isolation is implemented to ensure that the applications and/or data of different tenants are not shared with each other. Various tenant isolation approaches may be used. In an embodiment, each tenant is associated with a tenant ID. Applications implemented by the computer network are tagged with tenant ID's. Additionally or alternatively, data structures and/or datasets, stored by the computer network, are tagged with tenant ID's. A tenant is permitted access to a particular application, data structure, and/or dataset only if the tenant and the particular application, data structure, and/or dataset are associated with a same tenant ID. As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants. A subscription list may indicate which tenants have authorization to access which applications. For each application, a list of tenant ID's of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels may be used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

What is claimed is:

1. One or more non-transitory computer-readable media storing instructions that, when executed by one or more processors, cause performance of operations comprising:
   obtaining, from a user, a plurality of values of fields of a healthcare form, including obtaining at least a subset of the plurality of values via a user interface of a first device operated by the user;
   transferring a workflow for preparing a form bundle from the user interface of the first device to a user interface of a second device operated by the user;
   in response to transferring the workload, capturing a live image comprising supplemental documentation for the healthcare form, from a camera of the second device operated by the user;
   generating, by the second device, the form bundle comprising (a) an electronic version of the healthcare form populated with the plurality of values, and (b) the image comprising the supplemental documentation for the healthcare form; and
   responsive to user input to the user interface of the second device, transmitting the form bundle from the second device to a healthcare organization.

2. The one or more non-transitory computer-readable media of claim 1, wherein transferring the workflow includes:
   Responsive to user input to the user interface of the first device, sending a message to the second device comprising a link to a website for capturing the live image.

3. The one or more non-transitory computer-readable media of claim 2, wherein transferring the workflow further includes:
   obtaining, via the user interface of the second device, contact information associated with the second device; and
   initiating an authentication process for the contact information associated with the second device,
   wherein sending the message to the second device is performed only upon successful completion of the authentication process for the contact information associated with the second device.

4. The one or more non-transitory computer-readable media of claim 3, wherein obtaining the plurality of values of fields of the healthcare form comprises obtaining the contact information associated with the second device.

5. The one or more non-transitory computer-readable media of claim 1, wherein the second device operated by the user is a mobile device.

6. A system comprising:
   a first device including a hardware processor and a user interface; and
   a second device including a hardware processor, a user interface, and a camera;
   the system being configured to perform operations comprising:
      obtaining, from a user, a plurality of values of fields of a healthcare form, including obtaining at least a subset of the plurality of values via the user interface of the first device operated by the user;
      transferring a workflow for preparing a form bundle from the user interface of the first device to the user interface of the second device;
      in response to transferring the workload, capturing a live image comprising supplemental documentation for the healthcare form, from the camera of the second device operated by the user;
      generating, by the second device, the form bundle comprising (a) an electronic version of the healthcare form populated with the plurality of values, and (b) the image comprising the supplemental documentation for the healthcare form; and
      responsive to user input to the user interface of the second device, transmitting the form bundle from the second device to a healthcare organization.

7. The system of claim 6, wherein transferring the workflow includes:
   responsive to user input to the user interface of the first device, sending a message to the second device comprising a link to a website for capturing the live image.

8. The system of claim 7, wherein transferring the workflow further includes:

obtaining, via the user interface of the second device, contact information associated with the second device; and initiating an authentication process for the contact information associated with the second device, wherein sending the message to the second device is performed only upon successful completion of the authentication process for the contact information associated with the second device.

9. The system of claim 8, wherein obtaining the plurality of values of fields of the healthcare form comprises obtaining the contact information associated with the second device.

10. The system of claim 6, wherein the second device operated by the user is a mobile device.

11. A method comprising:
obtaining, from a user, a plurality of values of fields of a healthcare form, including obtaining at least a subset of the plurality of values via a user interface of a first device operated by the user;

transferring a workflow for preparing a form bundle from the user interface of the first device to a user interface of a second device operated by the user;

in response to transferring the workload, capturing a live image comprising supplemental documentation for the healthcare form, from a camera of the second device operated by the user;

generating, by the second device, the form bundle comprising (a) an electronic version of the healthcare form populated with the plurality of values, and (b) the image comprising the supplemental documentation for the healthcare form; and responsive to user input to the user interface of the second device, transmitting the form bundle from the second device to a healthcare organization.

12. The method of claim 11, wherein transferring the workflow includes:
responsive to user input to the user interface of the first device, sending a message to the second device comprising a link to a website for capturing the live image.

13. The method of claim 12, wherein transferring the workflow further includes:
obtaining, via the user interface of the first device, contact information associated with the second device; and initiating an authentication process for the contact information associated with the first second device, wherein sending the message to the second device is performed only upon successful completion of the authentication process for the contact information associated with the second device.

14. The method of claim 13, wherein obtaining the plurality of values of fields of the healthcare form comprises obtaining the contact information associated with the second device.

15. The method of claim 11, wherein the method further comprises:
displaying (a) the electronic version of the healthcare form populated with the plurality of values, and (b) the image comprising the supplemental documentation for the healthcare form to the user via the user interface of the second device; and in response to receiving an update to one of the plurality of values from the user via the user interface of the second device, changing that value of the plurality of values.

* * * * *